US007649088B2

(12) United States Patent
Fink et al.

(10) Patent No.: US 7,649,088 B2
(45) Date of Patent: Jan. 19, 2010

(54) ATLASTIN

(75) Inventors: John K. Fink, Ann Arbor, MI (US); Xinping Zhao, Houston, TX (US)

(73) Assignee: The Regents of the University of Michigan, Ann Arbor, MI (US)

( * ) Notice: Subject to any disclaimer, the term of this patent is extended or adjusted under 35 U.S.C. 154(b) by 107 days.

(21) Appl. No.: 11/523,305

(22) Filed: Sep. 19, 2006

(65) Prior Publication Data

US 2007/0015202 A1    Jan. 18, 2007

Related U.S. Application Data

(62) Division of application No. 10/242,008, filed on Sep. 12, 2002, now Pat. No. 7,108,975.

(60) Provisional application No. 60/323,997, filed on Sep. 21, 2001.

(51) Int. Cl.
C07H 21/02 (2006.01)
C07H 21/04 (2006.01)
(52) U.S. Cl. .................... 536/23.5; 536/23.1; 536/23.2; 536/24.31; 435/320.1
(58) Field of Classification Search .................. None
See application file for complete search history.

(56) References Cited

U.S. PATENT DOCUMENTS

| 4,366,241 | A | 12/1982 | Tom et al. |
| 4,435,504 | A | 3/1984 | Zuk et al. |
| 4,650,764 | A | 3/1987 | Temin et al. |
| 4,657,760 | A | 4/1987 | Kung et al. |
| 4,980,289 | A | 12/1990 | Temin et al. |
| 5,124,263 | A | 6/1992 | Temin et al. |
| 5,206,344 | A | 4/1993 | Katre et al. |
| 5,225,212 | A | 7/1993 | Martin et al. |
| 5,399,346 | A | 3/1995 | Anderson et al. |
| 5,474,796 | A | 12/1995 | Brennan |
| 5,538,848 | A | 7/1996 | Livak et al. |
| 5,580,859 | A | 12/1996 | felgner et al. |
| 5,589,466 | A | 12/1996 | Felgner et al. |
| 5,605,789 | A | 2/1997 | Chen et al. |
| 5,719,208 | A | 2/1998 | Wideman et al. |
| 5,733,731 | A | 3/1998 | Schatz et al. |
| 5,777,324 | A | 7/1998 | Hillenkamp |
| 5,811,238 | A | 9/1998 | Stemmer et al. |
| 5,830,721 | A | 11/1998 | Stemmer et al. |
| 5,837,458 | A | 11/1998 | Minshull et al. |
| 5,843,654 | A | 12/1998 | Heisler et al. |
| 5,843,669 | A | 12/1998 | Kaiser et al. |
| 5,846,717 | A | 12/1998 | Borw et al. |
| 5,858,695 | A | 1/1999 | Kadota et al. |
| 5,888,780 | A | 3/1999 | Dahlberg et al. |
| 5,919,626 | A | 7/1999 | Shi et al. |
| 5,925,525 | A | 7/1999 | Fodor et al. |
| 5,952,174 | A | 9/1999 | Nikiforov et al. |
| 5,985,551 | A | 11/1999 | Brennan |
| 5,985,557 | A | 11/1999 | Prudent et al. |
| 5,994,069 | A | 11/1999 | Hall et al. |
| 6,001,567 | A | 12/1999 | Brow et al. |
| 6,017,696 | A | 1/2000 | Heller |
| 6,043,031 | A | 3/2000 | Koster et al. |
| 6,045,996 | A | 4/2000 | Cronin et al. |
| 6,051,380 | A | 4/2000 | Sosnowski et al. |
| 6,068,818 | A | 5/2000 | Ackley et al. |
| 6,090,543 | A | 7/2000 | Prudent et al. |
| 6,125,383 | A | 9/2000 | Glynias et al. |
| 6,312,922 | B1 * | 11/2001 | Edwards et al. ............. 435/69.1 |
| 6,582,908 | B2 * | 6/2003 | Fodor et al. .................... 506/9 |

FOREIGN PATENT DOCUMENTS

| EP | 025949 | 4/1981 |
| EP | 178220 | 4/1986 |
| EP | 453242 | 10/1991 |
| WO | WO 90/08832 | 8/1990 |
| WO | WO 93/03176 | 2/1993 |
| WO | WO 94/26914 | 11/1994 |
| WO | WO 95/07358 | 3/1995 |
| WO | PCT/US95/14575 | 11/1995 |
| WO | 00/37630 | * 6/2000 |
| WO | WO 03/026566 | 4/2003 |

OTHER PUBLICATIONS

GenBank Accession No. AL606834. Sep. 19, 2001. NCBI Database, National Library of Medicine, NIH (Bethesda, MD, USA).*
Human Organized Whole Genome Database (HOWDY) for SPG3A gene, available via url: <http://howdy.jst.go.jp/HOWDYCL// HOWDY.pl?Cls=Marker&Key=UKEY&Val=87092>.*
Osoegawa et al. Genomics. 1998. 52: 1-8.*
Peter de Jong email letter (Jun. 12, 2002).*
Genecard for Atlastin/SPG3A. Available via url: <genecards.org/cgi-bin/carddisp.pl?gene=SPG3A&search=neurodegenerative%20or%20senile&asd=6>.*
Strausberg, R. NCBI Database, National Library of Medicine, NIH (Bethesda, MD, USA), NCBI Accession No. BE781422, Sep. 20, 2000.*
Buck et al. Biotechniques, 1999, 27:528-536.*
Alvarado et al., "Atlastin gene analysis in early onset hereditary spastic paraplegia," American Journal of Human Genetics 69:597 (2001).
D'Amica et al., Neurology, 2004, 62:2138-2139.
Dalpozzo et al., Neurology, 2003, 61:580-581.
Durr et al., Archives Neurology, 2004, 61:1867-1872.

(Continued)

Primary Examiner—Carla Myers
(74) Attorney, Agent, or Firm—Casimir Jones SC

(57) ABSTRACT

The present invention relates to methods and compositions of a novel gene and the peptide encoded by the gene. Mutations in the gene, named atlastin, are factors in the disease Hereditary Spastic Paraplegia and related disorders. The present invention will be used for the in the research, diagnosis and treatment of these disabling diseases.

7 Claims, 3 Drawing Sheets

OTHER PUBLICATIONS

International Search Report for PCT/US02/029165 dated Apr. 22, 2004.
International Search Report for PCT/US2004/004013 dated Aug. 23, 2004.
Wang et al., Proc. Natl. Acad, Sci. U.S.A. 91:8180-8184.
Williams et al. (1991) Proc. Natl. Acad. Sci. USA 88:2726.
Wu and Wu (1987) J. Biol. Chem., 262:4429-4432.
Wu and Wu (1988) J. Biol. Chem., 263:14621-14624.
Wilson et al. (1992) J. Biol. Chem., 267-963-967.
Zhang et al. (1997) Proc. Natl. Acad. Sci. USA, 94:4504.
Zhao et al. "Mutations in a newly identified GTPase gene cause autosomal dominant hereditary spastic paraplegia" Nature Genetics. Nov. 2001, vol. 29, pp. 326-331.
Muglia et al. "Further evidence that SPG3A gene mutations cause autosomal dominant hereditary spactic paraplegia" Annals of Neurology. Jun. 2002, vol. 51, No. 6, pp. 794-79.
Zhao et al., "Homo spaiens GTPase mRNA complete cds" (Feb. 12, 2002) Abstract, Database accession No. A032844.
Tessa et al., "SPG3A: An additional family carrying a new alastin mutation," Neurology 59:2002-2005 (2002).
Christopherson et al., Proc. Natl. Acad, Sci. U.S.A. 89:6314-6318 (1992).
Sauter et al., Human Mutation 23:98 (2004).
Gossen et al., Proc. Natl. Acad. Sci. U.S.A. 89:5547-5551 (1992).
Huang et al. (1988) J. Viral., 62:3855.
Janknecht et al., Proc. Natl. Acad. Sci. U.S.A. 88:8972.
Zhu et al., Journal of Biological Chemistry 278:49063-49071 (2003).
Markowitz et al. (1988) J. Virol., 62:1120.
Posnett et al. (1988) J. Biol. Chem. 263:1719.
Schlienger et al. (1992) J. Virol, 66:2570-2576.
Stemmer (1994) Proc. Natl. Acad. Sci. USA, 91:10747.
US 5,962,233, 10/1999, Livak et al. (withdrawn)

* cited by examiner

```
Exon 1
  1 CCCTTTTCCTCCCCACTCCTTCCCACCAGCGCCACCAGCAACATCCTCAGAGTCTGAGCGAACTGGCCCAGCGGGGCACGGAGCCTCCC
 91 ACCGCCAGCAACCTGCGCCCCGAGAAGGCAGCGAGCCAGTGACAGCCTCACCGCCAGCTCCTGACCCAGTCCTCCTGACCACCATGGCCAAGAAC
                                                                              M  A  K  N    4
    Exon 2
181 CGCAGGGACAGAACAGTTGGGTGAATTTCGAAAGACATATGAGTCAGAGAGACCAGTGAAAAAGGCAGGACCA
    R  R  D  R  N  S  W  G  G  F  S  E  K  T  Y  E  W  S  S  E  E  E  P  V  K  K  A  G  P   34
                            5                        6                9
271 GTCCAAGTCCTCATTGTCAAGATGACCATTCCTTTGAGTTAGATGAAACTGCATTAAATCGGATCCTTCTCGAGGTGTCAGAGAC
    V  Q  V  L  I  V  K  D  D  H  S  F  E  L  D  E  T  A  L  N  R  I  L  L  S  E  A  V  R  D   64
361 AAGGAGGTTGTTGCTGTATCTGTTGCTGGAGCATTAGAAAGGAAATCATT CCTGATGGACTTCATGTTGAGATACATGTACAACCAG
    K  E  V  V  A  V  S  V  A |G  A  F  R  G  K  S| F  L  M  D  F  M  L  R  Y  M  Y  N  Q    94
                              7                  1
    Exon 3
451 GAATCAGTTGATTGGGTTGGAGACTACAATGAACCATTGACTGGTTTTTCATGGAGAGGTGGATCTGAAAGAGAGGAATTCAG
    E  S  V  D  W  V  G  D  Y  N  E  P  L  T  G  F  S  W  R  G  G  S  E  R  E  T  T  G  I  Q   124
                                Exon 4  5                              5         6
541 ATATGGAGTGAAATCTTCCTATTCAATAAACCTGATGGTAAAAAGTTGCAGTTTATTGATGATACTCAGGGAACCTTTGATAGTCAG
    I  W  S  E  I  F  L  I  N  K  P  D  G  K  K  V  A  V  L  L  M |D  T  Q  G| T  F  D  S  Q   154
                                           8                       Exon 5  2         7
631 TCAACTTTGAGAGATTCAGCCACACTTCCCTTAGCACAAATCAGTCAATACAGCTACAAGTATATAACTTATCCCAAAATGTCAGAG
    S  T  L  R  D  S  A  T  V  F  A  L  S  T  M  I  S  S  I  Q  Y  N  L  S  Q  N  V  Q  E   184
       5        6                                     Exon 6
721 GATGATCTTCAGCACTTCCAGCTTTTTCACTGAGTATGGCAGAGTGGCAATTCAGAGTCTGATATTT
    D  D  L  Q  H  L  Q  L  F  T  E  Y  G  R  L  A  M  E  E  T  F  L  K  P  F  Q  S  L  I  F   214
                                                                               Exon 8
811 CTTGTTCGAGAGTTTCCAGATACGAATTTCATATGGAGCCCATGGTGTCCAAATTCTTGGAAAACGCCTCAAG TCTCAGG
    L  V |R  D| W  S  F  P  P  Y  E  F  F  S  Y  G  A  D  G  G  A  K  F  L  E  K  R  L  K  V  S  G   244
         3                                          7
901 AACCAGCATGAAGACTGAAGAACTACAGAACGTCAGAAAACACATTCATTCCTGTTTCACCAACATTCCTGTTTTCCTGTTCTACTCCATCCTGGCTTA
    N  Q  H  E  E  L  Q  N  V  R  K  H  I  H  S  C  F  T  N  I  S  C  F  L  L  P  H  P  G  L    274
                                                  4
991 AAAGTAGCTACCAATCCAAACTTTGATGGAAAATTGAAA GAATAGAAATCATCAAAAACTTGAAATACTTGATTCCTTGGCTA
    K  V  A  T  N  P  N  F  D  G  K  L |E| I  D  D  E  F  I  K  N  L  K  I  L  I  P  W  L    304
                      7
```

FIG. 2A

```
1081  CTTAGTCCCGAGAGCCTAGATATTAAAGAGATCAATGGAATAAATCACCTGCCGGGTCTGGTGGAGTACTTCAAG|Exon 10
                                                                              |CTTATATAAAG
      L  S  P  E  S  L  D  I  K  E  I  N  G  N  K  I  T  C  R  G  L  V  E  Y  F  K  A  Y  I  K   334

1171  ATCTATCAAGGTGAAGAATTACCACACTGCCAATCCCAAATCCATGTTACAG|Exon 11
                                                        |GCCACAGAAGCTAACAATTTAGCAGCCGTGGCAACTGCCAAG
      I  Y  Q  G  E  E  L  P  H  P  K  S  M  L  Q   A  T  A  E  A  N  N  L  A  A  V  A  T  A  K   364
                                                  7                                        5

1261  GACACAATACAACAAAAAATGAAGAGA|Exon 12
                                 |ATTTGTGGTGACAAATGACTTGCAGACCAAACACCTGCAACTT
      D  T  Y  N  K  K  M  E  E  I  C  G  G  D  K  P  F  L  A  P  N  D  L  Q  T  K  H  L  Q  L   394
         6

1351  AAGGAGAATCTGTGAAGCTATTCCGAGGGGTGAAGAAGATGGGTGAAGAATTTAGCCGGTTACCTGCAGCAGTTGGAGAGTGAA
      K  E  E  S  V  K  L  F  R  G  V  K  K  M  G  E  E  F  S  R  R  Y  L  Q  Q  L  E  S  E   424
                        5                                5                              6

1441  ATAGATGAACTTTACATCCAATATATCAAGCACAATGATAGCAAAAATATCTTCATGCAGCTCGTACCCCAGCACTGTTGTAGTC
      I  D  E  L  Y  I  Q  Y  I  K  H  N  D  S  K  N  I  F  H  A  A  R  T  P  A  T  L  F  V  V   454
         5                                4

1531  ATCTTTATCACATATGTCATTGCTGGGGTGACTGGATTCATTGGTTTGGACATCATAGCCTAGCCAATATGATAATGGGACTGACC
      I  F  I  T  Y  V  I  A  G  V  T  G  F  I  G  L  D  I  I  A  S  L  C  N  M  I  M  G  L  T   484

1621  CTTATCACCCTGTGCACTTGGGCATATATCCGTACCCTCTGGAGAGCTGGGAGCTGTAATAGACCAGTGGCTGCAGCTCTG
      L  I  T  L  C  T  W  A  Y  I  R  Y  S  G  E  Y  R  E  L  G  A  V  I  D  Q  V  A  A  A  L   514

1711  TGGGACCAG|Exon 13
                |GAAGTACAAAATGAG|Exon 14
                                 |CTTTGTTGTACAAGCTTTACATCGTATCATCAAGCTTTCCCTACA
      W  D  Q   G  S  T  N  E   A  L  Y  K  L  Y  S  A  A  A  T  H  R  H  L  Y  H  Q  A  F  P  T   544

1801  CCAAAGTCGAATCTACTGAACAATCAGAAGAAAAATGTAATGCAGGTGCATGACCAATTGTCAATTAAA
      P  K  S  E  E  S  T  E  Q  S  E  K  K  K  M                                                   558

1891  TATTCAGTTTTAGTCTTCCATGCAAACATTCAAACATTCAAACTTCTGAAGACTGCAAACTGA

1981  TTAGTTCTTTTACTTCAGTGTTTAATAAGCAGATGATGCATGTTATACTATTTGTTAACATGTACAATTTCCTGATTTTCTT

2071  CAAAAATGCTGTTTATAAGTATTTGTCTATTTATGATAACAGTACACGTGTTCTGCTTGAATTTACTAAATTCTACTACTGGGTTATAAT

2161  TAAATCAATGTGATATTCCAAAAAAAAAAAAAAAAAAAAAAAA
```

FIG. 2B

ATLASTIN

This application is a divisional of and claims priority to U.S. patent application Ser. No. 10/242,008, filed Sep. 12, 2002 now U.S. Pat. No. 7,108,975, which claims the benefit of U.S. Provisional Application No. 60/323,997, filed Sep. 21, 2001. The entire teachings of the above applications are incorporated herein by reference.

This invention was made in part with government support under grants 2RO1NS33645-05 and 1RO1NS38713 from the National Institutes of Health and a grant from the Department of Veterans Affairs. The government has certain rights in the invention.

FIELD OF THE INVENTION

The present invention relates to a novel gene named "atlastin" and its translated peptide product, as well as methods and compositions derived therefrom. More specifically, the present invention relates to the use of altastin for the diagnosis and treatment of Hereditary Spastic Paraplegia (HSP) and related diseases.

BACKGROUND

Hereditary spastic paraplegia (HSP) is characterized by insidiously progressive lower extremity weakness and spasticity that affects thousands of Americans and tens of thousands of individuals around the world. The disorder begins at any age. Wheelchairs are often required. HSP is classified as "uncomplicated" or "pure" if neurologic impairment is limited to progressive lower extremity spastic weakness, hypertonic urinary bladder disturbance, mild diminution of lower extremity vibration sensation and, occasionally, joint position sensation. HSP is classified as "complicated" if the impairments present in uncomplicated HSP are accompanied by other system involvement or other neurologic findings such as seizures, dementia, amyotrophy, extrapyramidal disturbance, or peripheral neuropathy, in the absence of other co-existing disorders such as diabetes mellitus.

Currently, the diagnosis of uncomplicated HSP is established by the presence of typical clinical features and the exclusion of alternative diagnostic possibilities. Clinical features of HSP include insidiously progressive, bilateral lower extremity weakness, and increased muscle tone that is maximal in the iliopsoas, hamstring, and tibialis anterior muscles; lower extremity hyperreflexia and extensor plantar responses, often accompanied by mildly impaired vibration sensation in the distal lower extremities; and family history of similarly affected individuals. Magnetic resonance imaging (MRI) of the brain and spinal cord may be normal or show thin corpus callosum and/or spinal cord atrophy. For the vast majority of subjects, hereditary spastic paraplegia is a diagnosis of exclusion. The differential diagnosis (including multiple sclerosis, structural abnormalities involving the spinal cord, B12 deficiency, adrenomyeloneuropathy and other leukodystrophies, and dopa-responsive dystonia) should be considered thoroughly.

Molecular genetic testing for mutations in the spastin and proteolipid protein (PLP) genes are available in a limited number of laboratories. Prenatal testing for other types of HSP is being investigated on a research basis.

As can be seen from the foregoing, at the present time, diagnosis of HSP is generally a process of exclusion of other disorders, and observation of family history. As with all types of exclusionary diagnosis, patients can and are misdiagnosed. What is needed is a test for the accurate diagnosis of HSP and new methods of treatment of this debilitating disease.

SUMMARY OF THE INVENTION

The present invention generally relates to compositions and methods for the diagnosis and treatment of Hereditary Spastic Paraplegia (HSP). It is not intended that the present invention be limited to particular method of diagnosis and treatment. The sequences of the present invention have been identified as a cause of HSP, a progressive and often paralyzing disease. There are different types of HSP. The gene of the present invention is located on chromosome 14 in a region known as the "SPG3 locus". The present invention provides compositions and methods that advance the development of treatments for degenerative neurological disorders such as HSP and other spinal cord disorders including spinal cord injury and amyotrophic lateral sclerosis.

In one embodiment, the present invention contemplates an isolated nucleic acid encoding at least a fragment of the atlastin gene (SEQ ID NO: 1) or protein (SEQ ID NO: 2) set forth in FIGS. 2A and 2B, including native and mutant sequences (e.g., atlastin containing one or more polymorphisms). Although the present invention is not limited to any particular mechanism and an understanding of the mechanism is not required to practice the present invention, atlastin contains inter-species conserved motifs (P-loop, DxxG motif and RD loop) that together characterize guanine binding/GTPase active sites. Atlastin's primary sequence and secondary structure show significant homology with several GTPases.

In another embodiment, said nucleic acid encodes a polypeptide fragment. It is not intended that the present invention be limited by the nature or size of the fragment. In yet another embodiment, said nucleic acid encodes a fusion protein. Additionally, the present invention relates to isolated sequences that comprise a mutation of the atlastin gene and are designated SEQ ID NOS: 3, 4 and 5.

It is not intended that the present invention be limited as to the specific nature of the nucleic acid encoding the peptides described above, (i.e. the "transgene") or portions thereof. In one embodiment, said nucleic acid is contained in a vector. In another embodiment, said vector is in a host cell. In yet another embodiment, said vector is in a transgenic animal. Additionally, said gene may integrate into the genome of the transgenic animal. In a particular embodiment, the transgenic animal of the present invention may be generated with the transgene contained in an inducible, tissue specific promotor.

The present invention also contemplates RNA transcribed from the above-indicated cDNA as well as protein (typically purified protein) translated from this RNA. Moreover, the present invention contemplates antibodies produced from immunizing with this translated protein.

Although embodiments of the present invention are not limited to any particular use or theory, the discovery of atlastin gene mutations as the cause of SPG3-linked HSP provides the ability to diagnose HSP and provide genetic counseling. Since SPG3-linked HSP represents ~9% of autosomal dominant HSP, testing for atlastin gene mutations permits laboratory diagnosis for this form of autosomal dominant HSP. Moreover, the observation that atlastin mutations in three of eleven early-onset ADHSP kindreds suggests that mutations in this gene are a relatively common cause of ADHSP that begins in childhood. Analysis of normal and mutant atlastin function provides insight into the molecular pathophysiology of SPG3-linked HSP and other related neurodegenerative disorders.

The present invention also contemplates using the above-named compositions in screening assays. The present invention is not limited by the particular method of screening. In one embodiment cells are used such as, but not limited to, transformed cell lines. In another embodiment primary cells may be used. The present invention is not limited to the nature of the transfection construct. The transfection constructs utilized are the optimal constructs available for the cell line chosen at the time of setting up the assay. In one embodiment, the present invention contemplates screening suspected compounds (e.g., drug candidates) in a system utilizing transfected cell lines. In one embodiment, the cells are transfected transiently. In another embodiment, the cells are stably transfected. In yet another embodiment translation products of the invention are used in a cell-free assay system. In yet another embodiment, antibodies generated to the translation products of the invention are used in immunoprecipitation assays or used in vivo.

Furthermore, the present invention is also used to identify atlastin binding partners and interactive proteins. In one embodiment, antibodies generated to translation products of the invention are used in immunoprecipitation experiments to isolate peptides that interact with atlastin. In another embodiment, the invention is used to generate fusion proteins that are used to isolate interactive proteins. In yet another embodiment, screens are conducted using the yeast two-hybrid system.

In another embodiment, peptides of the invention is used in microchip assays. For example, the present invention contemplates a method of screening, comprising: a) providing in any order: i) a first solid support (e.g. microchip) comprising peptides or peptide fragments from a library of the species to be examined and ii) a peptide, or portion thereof, encoded by the DNA of SEQ ID NO:1; b) contacting said microassay microchips with said peptide under conditions such that binding occurs.

The present invention is also used to identify new homologs of atlastin or natural mutations thereof. The present invention contemplates screening for homologs using standard molecular procedures. In one embodiment screens are conducted using Northern and Southern blotting.

The present invention contemplates a method of screening a compound, said method comprising: a) providing in any order: i) a first group of cells comprising a recombinant expression vector, wherein said vector comprises at least a portion of the oligonucleotide sequence of SEQ ID NO:1, ii) and a test compound; b) contacting said first and second groups of cells with said compound; and c) detecting the effects of said compound. This method may also be used with SEQ ID NOS: 3, 4 and 5. In another embodiment, the effects of the compound are detected by screening for GTPase activity by methods know to those practiced in the art. In still another embodiment, a second group of cells comprise a recombinant expression vector, wherein said vector comprises a suitable control (e.g., an empty vector).

The present invention also contemplates a method of screening for homologs, said method comprising: a) providing in any order: i) a nucleic acid comprising at least a portion of the sequence of SEQ ID NO:1, and ii) DNA libraries from cells or tissues suspected to comprise said homolog; and b) hybridizing said first or second nucleic acid with said DNA of said library under conditions such that said DNA suspected of coding for said homolog is detected. This method may also be used with SEQ ID NOS: 3, 4 and 5.

The present invention also contemplates a method of screening for interactive peptides, said method comprising: a) providing in any order: i) a peptide comprising at least a portion of the peptide sequence of SEQ ID NO: 2 (including but not limited to portions that are part of fusion proteins, e.g., proteins that contain another portion, such as a portion useful for protein purification) and b) an extract from source (e.g., cells or tissues) suspected of having said interactive peptides; and c) mixing said peptide with said extract under conditions such that said interactive peptide is detected. This method may also be used with at least a portion of the translation products of SEQ ID NOS: 3, 4 and 5.

The present invention also contemplates an approach for screening for interactive peptides, said method comprising: a) providing in any order: i) antibodies reactive with (e.g., specific for) at least a portion of a peptide having the sequence of SEQ ID NO: 2, and ii) an extract from a source (e.g. cells or tissues) suspected of having said interactive peptide(s); and b) mixing said antibody with said extract under conditions such that said interactive peptide is detected. This method may also be used with antibodies reactive with at least a portion of the translation products of SEQ ID NOS: 3, 4 and 5.

The present invention contemplates the generation of cell lines that express the atlastin gene, or portion thereof. The present invention is not limited to any particular cell line (e.g., neuronal or non-neuronal cells).

The present invention contemplates DNA binding assays where a) atlastin DNA (e.g., SEQ ID NO:1), or portion thereof, is either i) adhered to a solid support surface or ii) placed in a suspension, b) compounds suspected of binding to the DNA are added in a manner that promotes binding and c) binding is measured. Detection methods utilized include, but are not limited to, staining, gel electrophoresis and spectrophometric methods. This method may also be used with at least portions of SEQ ID NOS: 3, 4 and 5.

The present invention contemplates high throughput screening methods. Such methods include, but are not limited to, DNA array assays, spectrophotometric assays, mass spectometry, the use of robotics, the use of computerized assay systems and the use of commercially available systems.

The present invention contemplates screening for proteins that bind to atlastin binding sites. The present invention is not limited to any particular assay method. In one embodiment, DNA encoding the sequences of the present invention (proteins encoded by SEQ ID NOS: 1, 3, 4 and 5 or portions thereof) is attached to a solid surface (e.g., a microchip) and protein suspected of binding the DNA sequences is placed in contact with the DNA. Attached proteins are then analyzed by methods know to those in the art.

The present invention contemplates prenatal testing for mutant atlastin genes. Such techniques are known in the art. For example, parents or fetuses can be screened for mutant atlastin alleles.

The present invention contemplates a method, comprising: a) providing in any order: i) a first solid support comprising nucleic acid from a DNA library of the species to be examined and ii) an oligonucleotide, selected form a group consisting of SEQ ID NOS:1, 3, 4 and 5 and portions thereof; b) contacting said solid support with said oligonucleotide under conditions such that hybridization takes place. In one embodiment, the present invention contemplates the solid support is a microchip.

The present invention contemplates a method of screening a compound, said method comprising: a) providing in any order: i) a first group of cells comprising a recombinant expression vector, wherein said vector comprises at least a portion of the an oligonucleotide, selected form a group consisting of SEQ ID NOS:1, 3, 4 and 5 and portions thereof, ii) a second group of cells comprising a recombinant expression vector, wherein said vector comprises an empty vector, and iii) a test compound; b) contacting said first and second groups of cells with said compound to produce seronergic receptor generating cells or serotonin releasing cells; and c) culturing said cells under conditions such that said seronergic receptor generation or serotonin release is detected.

The present invention contemplates a method of screening for homologs, said method comprising: a) providing in any order: i) a nucleic acid comprising at least a portion of an oligonucleotide, selected form a group consisting of SEQ ID NOS:1, 3, 4 and 5 and portions thereof, and ii) DNA libraries from cells or tissues suspected to comprise said homolog; and b) hybridizing said first or second nucleic acid with said DNA of said library under conditions such that said DNA suspected of coding for said homolog is detected.

The present invention contemplates a method comprising: a) providing in any order: i) a peptide comprising at least a portion of the peptide sequence of SEQ ID NO: 2 and ii) an extract from source suspected of having one or more interactive peptides; and c) mixing said peptide with said extract under conditions such that said one or more interactive peptides is detected. In one embodiment, the peptide is a fusion protein.

The present invention contemplates a method comprising: a) providing in any order: i) antibodies reactive with at least a portion of a peptide having the sequence of SEQ ID NO: 2, and ii) an extract from a source suspected of having one or more interactive peptides; and b) mixing said antibody with said extract under conditions such that said one or more interactive peptides is detected. In one embodiment, the peptide is a fusion protein.

In one embodiment, the present invention contemplates a method of identifying subjects who have HSP and those at risk of developing HSP comprising: a) providing nucleic acid from a subject, wherein the nucleic acid comprises a atlastin gene; and b) detecting the presence or absence of one or more variations in the atlastin gene. In another embodiment, the present invention contemplates the additional step of c) determining if the subject is at risk of developing HSP based on the presence or absence of the one or more variations. In yet another embodiment, the present invention contemplates that the variation is a single nucleotide polymorphism. In yet another embodiment, the present invention contemplates that the variation causes a frameshift mutation in atlastin. In yet another embodiment, the present invention contemplates that the variation causes a splice mutation in atlastin. In yet another embodiment, the present invention contemplates that the variation causes a nonconservative amino acid substitution, insertion and deletion in atlastin. In yet another embodiment, the present invention contemplates that variation is selected from the group consisting of the mutations shown in Table 1. In yet another embodiment, the present invention contemplates that the detecting in step b) is accomplished by hybridization analysis. In yet another embodiment, the present invention contemplates that the detecting in step b) comprises comparing the sequence of the nucleic acid to the sequence of a wild-type atlastin nucleic acid.

In one embodiment, the present invention contemplates that A method of identifying subjects who have HSP and those at risk of developing HSP comprising: a) providing a blood sample from a subject, wherein the blood sample comprises an atlastin protease; and b) detecting the presence or absence of one or more variants of the atlastin protease. In another embodiment, the present invention contemplates that the detecting in step b) is accomplished by an antibody assay.

In one embodiment, the present invention contemplates a kit for determining if a subject has HSP or is at risk of developing HSP comprising a detection assay, wherein the detection assay is capable of specifically detecting a variant atlastin allele. In another embodiment, the present invention contemplates that a kit wherein the detection assay comprises a nucleic acid probe that hybridizes under stringent conditions to a nucleic acid sequence comprising at least one mutation selected from the group consisting of the mutations shown in Table 1.

In one embodiment, the present invention contemplates a kit for determining if a subject has HSP or is at risk of developing HSP comprising a detection assay, wherein the detection assay is capable of specifically detecting a variant atlastin GTPase. In another embodiment, the present invention contemplates a kit of wherein the detection assay comprises an antibody capable of binding to an atlastin selected from the group consisting of wild-type atlastin and atlastin comprising at least one amino acid mutation.

In one embodiment, the present invention contemplates an isolated nucleic acid comprising a sequence encoding a polypeptide selected from the group consisting of SEQ ID NO: 1, 3, 4 and 5. In another embodiment, the present invention contemplates that the nucleic acid sequence is operably linked to a heterologous promoter. In yet another embodiment, the present invention contemplates that a nucleic acid sequence, wherein the sequence is contained within a vector. In yet another embodiment, the present invention contemplates a host cell comprising the vector of the previous embodiment. In yet another embodiment, the present invention contemplates the host cell of the previous embodiment, wherein the host cell is selected from the group consisting of animal and plant cells. In yet another embodiment, the present invention contemplates a host cell of the previous embodiment, wherein the host cell is located in an organism.

In one embodiment, the present invention contemplates an isolated nucleic acid sequence comprising a sequence selected from the group consisting of SEQ ID NOs: 1, 3, 4 and 5. In another embodiment, the present invention contemplates a computer readable medium encoding a representation of SEQ ID NOs: 1, 3, 4 and 5.

In one embodiment, the present invention contemplates an isolated polypeptide comprising the amino acid sequence of SEQ ID NO: 2. In another embodiment, the present invention contemplates a computer readable medium encoding a representation of the polypeptide of SEQ ID NO: 2.

In one embodiment, the present invention contemplates a method of identifying subjects at risk of carrying an allele for HSP comprising: a) providing nucleic acid from a subject, wherein the nucleic acid comprises a atlastin gene; and b) detecting the presence or absence of one or more variations in the atlastin gene. In another embodiment, the present invention contemplates the method, further comprising step c) determining if the subject is at risk of carrying HSP based on the presence or absence of the one or more variations.

In one embodiment, the present invention contemplates a method of treating a patient with HSP, comprising administering a therapeutically effective amount of an atlastin such that the symptoms of the disease are alleviated, wherein the atlastin is selected from the group consisting of: recombinant atlastin; synthetic atlastin; mutants, variants, fragments, and fusions of recombinant atlastin; and mutants, variants, fragments, and fusions of synthetic atlastin.

DESCRIPTION OF THE DRAWINGS

FIGS. 2A and 2B show the atlastin cDNA (SEQ ID NO:1) and peptide sequences (SEQ ID NO: 2).

DEFINITIONS

Figure 1:
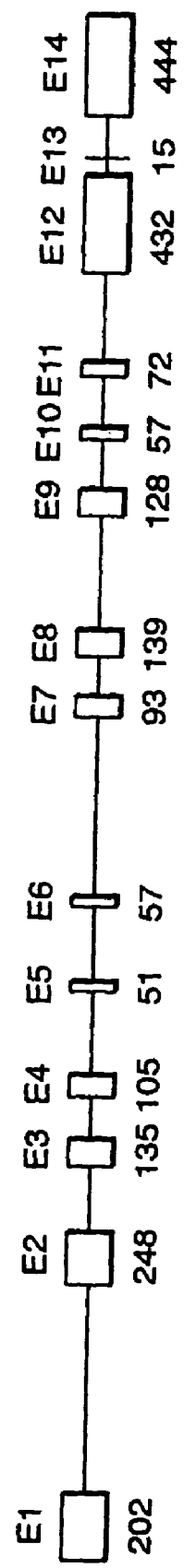
FIG. 1 shows atlastin genomic organization. The atlastin coding sequence spans ~69 kb genomic DNA and is divided into 14 exons. Exon length (bp) is shown.

In order to better understand the invention, the following definitions are provided.

"Hereditary spastic paraplegia (HSP)" is defined as a clinically and genetically diverse group of disorders in which the predominant symptom is insidiously progressive lower extremity weakness and spasticity. Other names for this family of diseases are listed below and are considered to by synonyms of HSP herein.

FSP—familial spastic paraplegia or familial spastic paraparesis

HSP—hereditary spastic paraplegia or hereditary spastic paraparesis

Strümpell Disease

Strümpell-Lorrain-Disease

Spastic Spinal Paralysis

Diplegia spinalis progressiva

Spastic Paraplegia

Hereditary progressive spastic paraplegia

SPG—Spastic paraplegia

SSP—Spastic spinal paralysis

Troyer Syndrome (A particular variant of complicated HSP)

Silver syndrome

Primary lateral sclerosis

Familial cerebral palsy

Familial diplegia

French Settlement Disease (FSD)

The term "at risk of developing HSP," or equivalent, refer to individuals that, because of genetic predisposition or environmental factors or both, have a higher propensity of developing HSP when compared to the population in general.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment; a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

In particular, the term "atlastin gene" refers to a full-length atlastin nucleotide sequence (e.g., as shown in SEQ ID NO:1). However, it is also intended that the term encompass fragments of the atlastin sequence, as well as other domains with the full-length atlastin nucleotide sequence. Furthermore, the terms "atlastin nucleotide sequence" or "atlastin polynucleotide sequence" encompasses DNA, cDNA, and RNA (e.g., mRNA) sequences.

The term "heterologous" when used in reference to a gene refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise gene sequences that comprise cDNA forms of a gene; the cDNA sequences may be expressed in either a sense (to produce mRNA) or anti-sense orientation (to produce an anti-sense RNA transcript that is complementary to the mRNA transcript). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with gene sequences in the chromosome, or are associated with portions of the chromosome not found in nature (e.g., genes expressed in loci where the gene is not normally expressed).

The term "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci. (U.S.A)* 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+ 0.41$ (% G+C), when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42EC in a solution consisting of 5×SSPE (43.8 g/l NaCl, 6.9 g/l $NaH_2PO_4(H_2O)$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42EC when a probe of about 500 nucleotides in length is employed.

"Medium stringency conditions" when used in reference to nucleic acid hybridization comprise conditions equivalent to binding or hybridization at 42EC in a solution consisting of 5×SSPE (43.8 g/l NaCl, 6.9 µl $NaH_2PO_4(H_2O)$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42EC when a probe of about 500 nucleotides in length is employed.

"High stringency conditions" when used in reference to nucleic acid hybridization comprise conditions equivalent to binding or hybridization at 42EC in a solution consisting of 5×SSPE (43.8 g/l NaCl, 6.9 g/l $NaH_2PO_4(H_2O)$ and 1.85 g/l EDTA, pH adjusted to 7.4 with NaOH), 0.5% SDS, 5×Denhardt's reagent and 100 µµg/ml denatured salmon sperm DNA followed by washing in a solution comprising 0.1× SSPE, 1.0% SDS at 42EC when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

The term "polymorphic locus" refers to a genetic locus present in a population that shows variation between members of the population (i.e., the most common allele has a frequency of less than 0.95). Thus, "polymorphism" refers to the existence of a character in two or more variant forms in a population. A "single nucleotide polymorphism" (or SNP) refers a genetic locus of a single base which may be occupied by one of at least two different nucleotides. In contrast, a "monomorphic locus" refers to a genetic locus at which little or no variations are seen between members of the population (generally taken to be a locus at which the most common allele exceeds a frequency of 0.95 in the gene pool of the population).

A "frameshift mutation" refers to a mutation in a nucleotide sequence, usually resulting from insertion or deletion of a single nucleotide (or two or four nucleotides) which results in a change in the correct reading frame of a structural DNA sequence encoding a protein. The altered reading frame usually results in the translated amino-acid sequence being changed or truncated.

A "splice mutation" refers to any mutation that affects gene expression by affecting correct RNA splicing. Splicing mutation may be due to mutations at intron-exon boundaries which alter splice sites.

The term "detection assay" refers to an assay for detecting the presence or absence of a sequence or a variant nucleic acid sequence (e.g., mutation or polymorphism in a given allele of a particular gene, as e.g., atlastin gene), or for detecting the presence or absence of a particular protein (e.g., atlastin) or the structure or activity or effect of a particular protein (e.g., atlastin GTPase activity) or for detecting the presence or absence of a variant of a particular protein.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlain et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length.

Promoters may be tissue specific or cell specific. The term "tissue specific" as it applies to a promoter refers to a promoter that is capable of directing selective expression of a nucleotide sequence of interest to a specific type of tissue in the relative absence of expression of the same nucleotide sequence of interest in a different type of tissue. Tissue specificity of a promoter may be evaluated by, for example, operably linking a reporter gene to the promoter sequence to generate a reporter construct, introducing the reporter construct into the genome of such that the reporter construct is integrated into every tissue of the resulting transgenic, and detecting the expression of the reporter gene (e.g., detecting mRNA, protein, or the activity of a protein encoded by the reporter gene) in different tissues of the transgenic. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or inducible. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

In contrast, an "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York [1989] pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "transgene" refers to a foreign gene that is placed into an organism by the process of transfection. The term "foreign gene" refers to any nucleic acid (e.g., gene sequence) that is introduced into the genome of an organism by experimental manipulations and may include gene sequences found in that organism so long as the introduced gene does not reside in the same location as does the naturally-occurring gene.

The term "transgenic" when used in reference to a host cell or an organism refers to a host cell or an organism that contains at least one heterologous or foreign gene in the host cell or in one or more of cells of the organism.

The term "host cell" refers to any cell capable of replicating and/or transcribing and/or translating a heterologous gene. Thus, a "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976, 796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. [1989] *Molecular Cloning: A Laboratory Manual*, Cold Spring Harbor Press, NY, pp 9.31-9.58).

The term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. [1989] supra, pp 7.39-7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "antigenic determinant" refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution. Compositions comprising polynucleotide sequences encoding atlastin (e.g., SEQ ID NO:2) or fragments thereof may be employed as hybridization probes. In this case, the atlastin encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "response," when used in reference to an assay, refers to the generation of a detectable signal (e.g., accumulation of reporter protein, increase in ion concentration, accumulation of a detectable chemical product).

The term "sample" is used in its broadest sense. In one sense it can refer to a animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

GENERAL DESCRIPTION OF THE INVENTION

Hereditary Spastic Paraplegia or Hereditary Spastic Paraparesis is a name used to represent a group of inherited degenerative spinal cord disorders characterized by a slow, gradual, progressive weakness and spasticity (stiffness) of the legs. Symptoms may be first noticed in early childhood, or at any age through adulthood. Initial symptoms may include difficulty with balance, weakness and stiffness in the legs, muscle spasms, and dragging the toes when walking. In some forms of the disorder, bladder symptoms (such as incontinence) may appear, or the weakness and stiffness may spread to other parts of the body. Rate of progression and the severity of symptoms is quite variable even among members of the same family. Anticipation may occur in some families, with symptoms of the disorder beginning earlier and more severely in successive generations. HSP rarely results in complete loss of lower limb mobility, although mobility devices such as canes, walkers, or wheelchairs may be necessary. In some patients, the symptoms continue to increase throughout their life. For others, symptoms may begin in early childhood, worsen for a few years, then level off after adolescence.

At the present time, diagnosis of HSP is generally a process of exclusion of other disorders, and observation of family history. However, a few of the gene locations have been found, and more are close to being identified. The atlastin gene of the present invention is a novel gene who's mutations are associated with this disease.

HSP causes the degeneration of the ends of the corticospinal tracts (also called upper motor neurons) within the spinal cord. These nerves begin in the motor cortex area of the brain, and end in the spinal cord. They synapse (connect) onto the spinal neurons (also called the lower motor neurons or anterior horn cells), which begin in the spinal cord and travel to the arms and legs. The cortico-spinal tracts that synapse with the nerves supplying the legs make their connection in the lower back, and are therefore much longer than the ones that synapse with the nerves supplying the arms, which make their connection in the neck. There is much more degeneration of the ends of the longest nerves (going to the legs) than there is in the ones going to the arms. Even though there is commonly some degeneration of the nerves supplying the arms, most people with HSP will not show any symptoms in the hands or arms.

In simple terms, the "nerves" consist of an axon (central core) surrounded by a coating known as the myelin sheath. This is similar to an electrical wire surrounded by a coating of insulation. The myelin is an insulator that helps the nerves conduct impulses faster. Some disorders with symptoms similar to HSP, such as multiple sclerosis, involve demyelination of the nerves. Although the present invention is not limited to any particular theory, in most cases of HSP it appears that the primary problem is not abnormal myelin, but a disturbance of the ends of the long axons, often with little or no loss of myelin.

Presently, there are some 15 gene loci associated with hereditary spastic paraplegia, of which only a few genes have been identified. The following lists some of the known loci, along with their associated links in the Genome Database.

Autosomal dominant: The most frequent gene locus is on chromosome 2p (the spastin gene) (SPG4). Other loci include those on chromosomes 2q (SPG13), chromosome 14q (SPG3A), chromosome 15q (SPG6), chromosome 8q (SPG8), chromosome 10q (SPG9), chromosome 12q (SPG10), and chromosome 19q (SPG12). Two X-linked variants have been identified in the genes for the L1 cell adhesion module (L1 CAM) on Xq28 (SPG1), and proteolipid protein (PLP) on Xq22 (SPG2). The recessive variant SPG5A was charted on chromosome 8. Recently, the locus for the paraplegin gene (SPG7) was charted on chromosome 16, which also contains SPG5B. Chromosome 15 contains SPG11. The present invention identifies a gene, atlastin, associated with HSP as well as three mutations that find use in diagnosis and treatment of the disease.

DETAILED DESCRIPTION OF THE PREFERRED EMBODIMENTS

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references [See, generally, Sambrook, et al., Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y.].

Oligonucleotides can be synthesized on an Applied BioSystems oligonucleotide synthesizer [for details see Sinha et al., Nucleic Acids Res. 12:4539 (1984)], according to specifications provided by the manufacturer. Complementary oligonucleotides are annealed by heating them to 90_C in a solution of 10 mM Tris-HCl buffer (pH 8.0) containing NaCl (200 mM) and then allowing them to cool slowly to room temperature. For binding and turnover assays, duplex DNA is purified from native polyacrylamide (15% w/v) gels. The band corresponding to double-stranded DNA is excised and soaked overnight in 0.30 M sodium acetate buffer (pH 5.0) containing EDTA (1 mM). After soaking, the supernatant is extracted with phenol/chloroform (1/1 v/v) and precipitated with ethanol. DNA substrates are radiolabeled on their 5'-OH group by treatment with [g-$^{32}$P]ATP and T4 polynucleotide kinase. Salts and unincorporated nucleotides are removed by chromatography on Sephadex G columns.

The present invention contemplates assays for detecting the ability of agents to inhibit or enhance atlastin function and atlastin binding where high-throughput screening formats are employed together with large agent banks (e.g., compound libraries, peptide libraries, and the like) to identify such antagonists or agonists and binding partners. Such atlastin antagonists and agonists and binding partners may be further developed as potential therapeutics and diagnostic or prognostic tools for diverse types of neurological and paraplegia diseases.

In embodiments of the present invention, the atlastin gene, and derivative products of the gene such as peptides, peptide fragments, antibodies, expression vectors and transgeneic animals, are useful for the diagnosis and treatment of an array of diseases that come under the family of Hereditary Spastic Paraplegias (HSP) and related diseases.

In other preferred embodiments, the atlastin gene, peptide or fragments thereof, can be used in an in vitro cell system for identifying other similar inhibitors peptides such as homologs. Also, the atlastin peptide fragments can be used to screen for peptides or other compounds that bind atlastin.

In yet other preferred embodiments, the atlastin gene, peptide or fragments thereof, can be used in the development of screening assays for the identification of individuals with atlastin mutations. Such assays, which are a vast improvement over traditional methods of diagnosis, will make the diagnosis of this disease easy and accurate.

Diagnostic Assays and Other Uses of the Invention

In preferred embodiments, the present invention provides the DNA encoding the protein atlastin, an important element in the etiology of HSP and related diseases.

In other embodiments, the invention provides nucleic acids encoding the atlastin polypeptide and atlastin fragments as part of expression vectors for introduction into cells. The invention provides methods of identifying intracellular or extracellular molecules which interact with atlastin or atlastin fragments, as well as exogenous agents (i.e., drugs) which disrupt the binding of atlastin and/or fragments thereof to such intracellular or extracellular targets.

The claimed polypeptide atlastin and atlastin fragments thereof, find particular use in screening assays for agents or lead compounds for agents useful in the diagnosis, prognosis or treatment of HSP and related diseases. One such assay involves forming mixtures of 1) atlastin (or fragments thereof) and 2) an atlastin-binding substrate, in the presence or absence of 3) a prospective drug candidate. The mixtures are made under conditions that permit the binding of the atlastin-binding substrate to atlastin (or fragments thereof) and the mixtures are then analyzed for the presence of such binding. A difference in such binding in the presence of such a drug candidate indicates that the agent is capable of modulating the binding of atlastin (or fragments thereof) to an atlastin-binding substrate. The assays of the present invention provide for facile high-throughput screening of compounds suspected to be able to inhibit such binding (e.g., compound libraries, peptide libraries, and the like) to identify potential drug candidates.

Atlastin and atlastin mutant screening methods, including cell-free methods and cellular methods, can be used in the practice of this invention. Cellular screening methods within the scope of this invention can involve transient expression vectors or stable transformation. Various atlastin and atlastin mutant screening protocols can be designed, according to well-known principles, by one of ordinary skill in the art. Soluble forms of atlastin and atlastin interaction partners can be utilized in cell free atlastin inhibitor screening protocols.

Preferably, atlastin inhibitor screening is carried out in a cellular system, using a reporter strain of cultured mammalian cells, transformed with one or more vectors encoding atlastin, and other assay components, as necessary.

Preferably, an atlastin-encoding sequence is cloned into a recombinant DNA vector, where it is expressed under the control of an inducible promoter, e.g., a heat shock promoter. [See, e.g., Wurm et al., *Proc. Natl. Acad. Sci. U.S.A.* 83:5414 (1986)]. Following induction of atlastin expression, cell death is measured in experimental treatments involving the presence of an inhibitor candidate, and in appropriate positive and negative controls.

Because overexpression of atlastin can be used to compensate for the expression of mutant atlastin in a patient and may be useful as a tool in gene therapy. Atlastin genes that may be used in gene therapy are preferably under the control of an exogenously regulatable promoter. An exogenously regulatable promoter is a promoter that can be induced by a specific set of environmental conditions, such as the increase in the concentration of a specific inducer. Examples of exogenously regulatable promoters and inducing conditions include: induction of a metallothionein promoter by zinc ions [Makarove et al., *Nucleic Acids Res.* 22:1504-1505 (1994)], removal of tetracycline, thereby activating a synthetic promoter based on the action of a tetracycline repressor-VP16 chimera [Gossen et al., *Proc. Natl. Acad. Sci. U.S.A.* 89:5547-5551 (1992)], addition of ecdysone [Christopherson et al., *Proc. Natl. Acad. Sci. U.S.A.* 89:6314-6318 (1992)], or the synthetic progesterone antagonist mifepristone [Wang et al., *Proc. Natl. Acad. Sci. U.S.A.* 91:8180-8184 (1994)].

Antibodies

The atlastin-encoding DNA of this invention enables one of ordinary skill in the art to produce anti-atlastin antibodies. The atlastin-encoding DNA is used to construct a vector encoding a fusion protein comprising an atlastin moiety and, preferably, an isolation-facilitating moiety, i.e., a moiety that can be readily isolated from contaminating proteins in an extract from a host cell used to express the fusion protein. A preferred isolation-facilitating moiety is maltose binding protein. DNA encoding maltose binding protein is commercially available. A binding reagent specific for the isolation-facilitating moiety is used for convenient and efficient isolation of the atlastin fusion protein. For example, amylose chromatography is preferred for isolation of a fusion protein comprising maltose binding protein moiety. Following isolation, the atlastin fusion protein is used to produce atlastin-specific antibodies (polyclonal or monoclonal), according to standard methods, known to a person skilled in the art.

The anti-atlastin antibodies of the invention have several uses. For example, they may be used as reagents for preparation of affinity chromatography media. Once the anti-atlastin antibodies of this invention are in hand, preparation of atlastin affinity chromatography media can be carried out according to conventional methods known to a person skilled in the art, using commercially available reagents. The atlastin-specific affinity chromatography media can be used to isolate full-length atlastin from natural sources or from host cells transformed with recombinant DNA encoding atlastin. The anti-atlastin antibodies of the invention are also useful as analytical-scale laboratory reagents for research on the physiology and cell biology of apoptosis. For example, immunohistochemical techniques, based on anti-atlastin monoclonal antibodies are likely to be valuable tools for embryologists seeking ways to observe the rate and/or distribution of apoptosis in the normal morphological development of metazoan animals.

The anti-atlastin antibodies of the invention are also useful as diagnostic immunoassay reagents for measuring atlastin levels in tissue samples from patients suspected of having an HSP-related disease or abnormality. Information on atlastin levels in selected cells or tissues is a useful diagnostic or prognostic indicator in any situation where following the progression of HSP-related diseases in important. The type of tissue sampled for the diagnostic test will vary, depending on the signs and symptoms of the patient and the suspected disease or abnormality.

If the tissue sample is highly homogenous with respect to cell type, it may be preferable to carry out the atlastin immunoassay on an extract from a homogenate. Alternatively, it may be preferable to use an immunohistochemical assay involving anti-atlastin antibodies. An immunohistochemical assay is preferable when the tissue sample is heterogenous with respect to cell type. An immunohistochemical assay will yield information on the distribution of differing atlastin levels in a cross section of tissue, or differing atlastin levels in other various types of cells.

The anti-atlastin antibodies of the present invention can be used in various diagnostic immunoassay formats known in the art. Exemplary immunoassay formats are competitive radioimmunoassay, ELISA, Western blot analysis and microcapillary devices comprising immobilized antibody. [See, e.g., Dafforn et al., *Clin. Chem.* 36:1312 (1990); Li et al., *Anal. Biochem.* 166:276 (1987); Zuk et al., U.S. Pat. No. 4,435,504; Zuk et al., *Clin. Chem.* 31:1144 (1985); Tom et al., U.S. Pat. No. 4,366,241; and Clark, PCT published application WO 93/03176].

Expression Vectors

The atlastin-encoding DNA of this invention can be used as an in situ hybridization reagent to assess transcription of atlastin genes and observe atlastin RNA processing, for diagnostic purposes or research purposes.

A wide variety of host/expression vector combinations can be employed for expressing atlastin-encoding DNA of this invention. The expression of atlastin-encoding DNA in a cellular screening assay is preferably in a eukaryotic cell, under the control of eukaryotic expression control sequences. More preferably, the eukaryotic cell is a cultured mammalian cell. Even more preferable, the mammalian cell is a human cell. If the expression of recombinant atlastin-encoding DNA is merely for the production of isolated recombinant atlastin, however, a prokaryotic host/expression vector system or a eukaryotic host/expression system can be used.

I. Atlastin Polynucleotides

As described above, a novel member of the dyamin family of large GTPases, atlastin, has been discovered. This was accomplished by studying a series of families in which HSP appears to be inherited and then using a positional cloning approach to map a gene responsible for reduced VWF-cleaving protease activity to a locus on 9q34. Accordingly, the present invention provides nucleic acids encoding atlastin and variants (e.g., polymorphisms and mutants), and fragments, including but not limited to, those described in SEQ ID NOs: 1, 3, 4 and 5. In some embodiments, the present invention provides polynucleotide sequences that are capable of hybridizing to SEQ ID NOs: 1, 3, 5, and 7 under conditions of low to high stringency as long as the polynucleotide sequence capable of hybridizing encodes a protein that retains at least one or a portion of at least one biological activity of a naturally occurring atlastin. In some embodiments, the protein that retains at least one or a portion of at least one biological activity of naturally occurring atlastin is 70% homologous to wild-type atlastin, preferably 80% homologous to wild-type atlastin, more preferably 90% homologous to wild-type atlastin, and most preferably 95% homologous to wild-type atlastin. In preferred embodiments, hybridization conditions are based on the melting temperature ($T_m$) of the nucleic acid binding complex and confer a defined "stringency" as explained above (See e.g., Wahl, et al., (1987) Meth. Enzymol., 152:399-407, incorporated herein by reference).

In other embodiments of the present invention, additional alleles of atlastin are provided. In preferred embodiments, alleles result from a polymorphism or mutation (e.g., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence. Non-limiting examples of the alleles of the present invention include those encoded by SEQ ID NOs: 1 (wild type), 3, 4, and 5, as well as those described in Tables 1 and 2.

In other embodiments of the present invention, the nucleotide sequences of the present invention may be engineered in order to alter an atlastin coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of atlastin may be extended utilizing the nucleotide sequences (e.g., SEQ ID NOs: 1, 3, 4 and 5) in various methods known in the art to detect upstream sequences such as promoters and regulatory elements. For example, it is contemplated that restriction-site polymerase chain reaction (PCR) will find use in the present invention. This is a direct method which uses universal primers to retrieve unknown sequence adjacent to a known locus (Gobinda et al. (1993) PCR Methods Applic., 2:318-22). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al. (1988) Nucleic Acids Res., 16:8186). The primers may be designed using Oligo 4.0 (National Biosciences Inc, Plymouth Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., (1991) Nucleic Acids Res., 19:3055-3060). The PROMOTERFINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed atlastin sequences are provided. In preferred embodiments, variants result from polymorphisms or mutations (e.g., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., atlastin GTPase function) for such purposes as altering (e.g., increasing or decreasing) the substrate specificity or selectivity affinity of the atlastin for VWF or another substrate. Such modified peptides are considered functional equivalents of peptides having an activity of atlastin as defined herein. A modified peptide can be produced in which the nucleotide sequence encoding the polypeptide has been altered, such as by substitution, deletion, or addition. In particularly preferred embodiments, these modifications do not significantly reduce the GTPase activity of the modified atlastin. In other words, construct "X" can be evaluated in order to determine whether it is a member of the genus of modified or variant atlastin's of the present invention as defined functionally, rather than structurally. In preferred embodiments, the activity of variant atlastin polypeptides is evaluated by the methods described in Example 1B.

Moreover, as described above, variant forms of atlastin and nucleotides encoding the same are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of atlastin disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a atlastin coding sequence including, but not limited to, alterations that modify the cloning, processing, localization, secretion, and/or expression of the gene product. Such mutations may be introduced using techniques that are well known in the art (e.g., site-directed mutagenesis to insert new restriction sites, alter glycosylation patterns, or change codon preference, etc.).

II. Atlastin Polypeptides

In other embodiments, the present invention provides atlastin polypeptides and fragments. Non-limiting examples of atlastin polypeptides (e.g., SEQ ID NO: 2) is shown in FIGS. 2A and 2B. Other embodiments of the present invention provide fusion proteins or functional equivalents of these atlastin proteins. In still other embodiments, the present invention provides atlastin polypeptide variants, homologs, and mutants. In some embodiments of the present invention, the polypeptide is a naturally purified product, in other embodiments it is a product of chemical synthetic procedures, and in still other embodiments it is produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or it may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NO:2 which encode substantially the same or a functionally equivalent amino acid sequences, may be used to clone and express atlastin. In general, such polynucleotide sequences hybridize to SEQ ID NO:1 under conditions of high to medium stringency as described above. As will be understood by those of skill in the art, it may be advantageous to produce atlastin-encoding nucleotide sequences possessing non-naturally occurring codons. Therefore, in some preferred embodiments, codons preferred by a particular prokaryotic or eukaryotic host (Murray et al. (1989) Nucl. Acids Res. 17) are selected, for example, to increase the rate of atlastin expression or to produce recombinant RNA transcripts having desirable properties, such as a longer half-life, than transcripts produced from naturally occurring sequence.

A. Vectors for Production of Atlastin

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOS: 1, 3, 4 and 5). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NO:1) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the E. coli lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in E. coli).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

B. Host Cells for Production of Atlastin

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines, T-1 (tobacco cell culture line), root cell and cultured roots in rhizosecretion (Gleba et al., Proc Natl Acad Sci USA 96: 5973-5977 [1999])

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al. (1986) Basic Methods in Molecular Biology). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al. (1989) Molecular Cloning: A Laboratory Manual, Second Edition, Cold Spring Harbor, N.Y.

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

C. Purification of Atlastin

The present invention also provides methods for recovering and purifying atlastin from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having the coding sequence (e.g., SEQ ID NOs: 1, 3, 4 and 5) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al. (1984) Cell, 37:767).

D. Fragments and Domains of Atlastin

In addition, the present invention provides fragments of atlastin (i.e., truncation mutants, e.g., portions of SEQ ID NOS:1, 3, 4 and 5). In other embodiments, the present invention provides domains of atlastin (e.g., the GTPase domain). In some embodiments of the present invention, when expression of a portion of the atlastin protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) J. Bacteriol., 169:751) and *Salmonella typhimurium* and its in vitro activity has been demonstrated on recombinant proteins (Miller et al. (1990) Proc. Natl. Acad. Sci. USA 84:2718). Therefore, removal of an N-terminal methionine, if desired, can be achieved either in vivo by expressing such recombinant polypeptides in a host which produces MAP (e.g., *E. coli* or CM89 or *S. cerevisiae*), or in vitro by use of purified MAP.

E. Fusion Proteins Containing Atlastin

The present invention also provides fusion proteins incorporating all or part of atlastin. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a atlastin protein. In some embodiments of the present invention, the VP6 capsid protein of rotavirus is used as an immunologic carrier protein for portions of the atlastin polypeptide, either in the monomeric form or in the form of a viral particle. In other embodiments of the present invention, the nucleic acid sequences corresponding to the portion of atlastin against which antibodies are to be raised can be incorporated into a fusion gene construct which includes coding sequences for a late vaccinia virus structural protein to produce a set of recombinant viruses expressing fusion proteins comprising a portion of atlastin as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of atlastin and the poliovirus capsid protein are created to enhance immunogenicity of the set of polypeptide antigens (See e.g., EP Publication No. 025949; and Evans et al. (1989) Nature 339:385; Huang et al. (1988) J. Virol., 62:3855; and Schlienger et al. (1992) J. Virol., 66:2).

In still other embodiments of the present invention, the multiple antigen peptide system for peptide-based immunization can be utilized. In this system, a desired portion of atlastin is obtained directly from organo-chemical synthesis of the peptide onto an oligomeric branching lysine core (see e.g., Posnett et al. (1988) J. Biol. Chem., 263:1719; and Nardelli et al. (1992) J. Immunol., 148:914). In other embodiments of the present invention, antigenic determinants of the atlastin proteins can also be expressed and presented by bacterial cells.

In addition to utilizing fusion proteins to enhance immunogenicity, it is widely appreciated that fusion proteins can also facilitate the expression of proteins, such as the atlastin protein of the present invention. Accordingly, in some embodiments of the present invention, atlastin can be generated as a glutathione-5-transferase (i.e., GST fusion protein). It is contemplated that such GST fusion proteins will enable easy purification of atlastin, such as by the use of glutathione-derivatized matrices (See e.g, Ausabel et al. (1992) (eds.), Current Protocols in Molecular Biology, John Wiley & Sons, NY). In another embodiment of the present invention, a fusion gene coding for a purification leader sequence, such as a poly-(His)/enterokinase cleavage site sequence at the N-terminus of the desired portion of atlastin, can allow purification of the expressed atlastin fusion protein by affinity chromatography using a $Ni^{2+}$ metal resin. In still another embodiment of the present invention, the purification leader sequence can then be subsequently removed by treatment with enterokinase (See e.g., Hochuli et al. (1987) J. Chromatogr., 411:177; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

F. Variants of Atlastin

Still other embodiments of the present invention provide mutant or variant forms of atlastin. It is possible to modify the structure of a peptide having an activity of atlastin for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject atlastin proteins as defined herein. A modified peptide can be produced in which the amino acid sequence has been altered, such as by amino acid substitution, deletion, or addition.

Moreover, as described above, variant forms (e.g., mutants or polymorphic sequences) of the subject atlastin proteins and the nucleotides encoding them are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present atlastin proteins, as well as truncation mutants, and is especially useful for identifying potential variant sequences (i.e., mutants or polymorphic sequences) that are functional in detecting mutant varients in vivo or in vitro. The purpose of screening such combinatorial libraries is to generate, for example, novel atlastin variants that can act as therapeutics.

Therefore, in some embodiments of the present invention, atlastin variants are engineered by the present method to provide altered substrate specificity or selectivity. In other embodiments of the present invention, combinatorially-derived variants are generated which have a selective potency relative to a naturally occurring atlastin. Such proteins, when expressed from recombinant DNA constructs, can be used in gene therapy protocols.

Still other embodiments of the present invention provide atlastin variants that have intracellular half-lives dramatically different than the corresponding wild-type protein. For example, the altered protein can be rendered either more stable or less stable to proteolytic degradation or other cellular process that result in destruction of, or otherwise inactivate atlastin. Such variants, and the genes which encode them, can be utilized to alter the location of atlastin expression by modulating the half-life of the protein. For instance, a short half-life can give rise to more transient atlastin biological effects and, when part of an inducible expression system, can allow tighter control of atlastin levels within the cell. Also, a long half-life can give rise to prolonged biological effects and have use as a therapeutic. As above, such proteins, and particularly their recombinant nucleic acid constructs, can be used in gene therapy protocols.

In some embodiments of the combinatorial mutagenesis approach of the present invention, the amino acid sequences for a population of atlastin homologs, variants or other related proteins are aligned, preferably to promote the highest homology possible. Such a population of variants can include, for example, atlastin homologs from one or more species, or atlastin variants from the same species but which differ due to mutation or polymorphisms. Amino acids that appear at each position of the aligned sequences are selected to create a degenerate set of combinatorial sequences.

In a preferred embodiment of the present invention, the combinatorial atlastin library is produced by way of a degenerate library of genes encoding a library of polypeptides which each include at least a portion of potential atlastin protein sequences. For example, a mixture of synthetic oligonucleotides can be enzymatically ligated into gene sequences such that the degenerate set of potential atlastin sequences are expressible as individual polypeptides, or alternatively, as a set of larger fusion proteins (e.g., for phage display) containing the set of atlastin sequences therein.

There are many ways by which the library of potential atlastin homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential atlastin sequences. The synthesis of degenerate oligonucleotides is well known in the art (See e.g., Narang (1983) Tetrahedron Lett., 39:39; Itakura et al. (1981) Recombinant DNA, in Walton (ed.), *Proceedings of the 3rd Cleveland Symposium on Macromolecules*, Elsevier, Amsterdam, pp 273-289; Itakura et al. (1984) Annu. Rev. Biochem., 53:323; Itakura et al. (1984) Science 198:1056; Ike et al. (1983) Nucl. Acid Res., 11:477). Such techniques have been employed in the directed evolution of other proteins (See e.g., Scott et al. (1980) Science 249:386; Roberts et al. (1992) Proc. Natl. Acad. Sci. USA 89:2429; Devlin et al. (1990) Science 249: 404; Cwirla et al. (1990) Proc. Natl. Acad. Sci. USA 87: 6378; as well as U.S. Pat. Nos. 5,223,409, 5,198,346, and 5,096, 815; each of which is incorporated herein by reference).

It is contemplated that the atlastin nucleic acids (e.g., SEQ ID NO:1, 3, 4 and 5, and fragments and variants thereof) can be utilized as starting nucleic acids for directed evolution. These techniques can be utilized to develop atlastin variants having desirable properties such as increased or decreased GTPase activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold (1996) Nat. Biotech., 14, 458; Leung et al. (1989) Technique, 1:11; Eckert and Kunkel (1991) PCR Methods Appl., 1:17-24; Caldwell and Joyce (1992) PCR Methods Appl., 2:28; and Zhao and Arnold (1997) Nuc. Acids. Res., 25:1307). After mutagenesis, the resulting clones are selected for desirable activity (e.g., screened for atlastin activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith (1994) Nature, 370: 324; U.S. Pat. Nos. 5,837,458; 5,830,721; 5,811,238; 5,733, 731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer (1994) Nature, 370:398; Stemmer (1994) Proc. Natl. Acad. Sci. USA, 91:10747; Crameri et al. (1996) Nat. Biotech., 14:315; Zhang et al. (1997) Proc. Natl. Acad. Sci. USA, 94:4504; and Crameri et al. (1997) Nat. Biotech., 15:436). Variants produced by directed evolution can be screened for atlastin activity by the methods described in Example 1B.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of atlastin homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

G. Chemical Synthesis of Atlastin

In an alternate embodiment of the invention, the coding sequence of atlastin is synthesized, whole or in part, using chemical methods well known in the art (See e.g., Caruthers et al. (1980) Nucl. Acids Res. Symp. Ser., 7:215; Crea and Horn (1980) Nucl. Acids Res., 9:2331; Matteucci and Caruthers (1980) Tetrahedron Lett., 21:719; and Chow and Kempe (1981) Nucl. Acids Res., 9:2807). In other embodiments of the present invention, the protein itself is produced using chemical methods to synthesize either an entire atlastin amino acid sequence or a portion thereof. For example, peptides can be synthesized by solid phase techniques, cleaved from the resin, and purified by preparative high performance liquid chromatography (See e.g., Creighton (1983) *Proteins Structures And Molecular Principles*, W H Freeman and Co, New York N.Y.). In other embodiments of the present invention, the composition of the synthetic peptides is confirmed by amino acid analysis or sequencing (See e.g., Creighton, supra).

Direct peptide synthesis can be performed using various solid-phase techniques (Roberge et al. (1995) Science 269: 202) and automated synthesis may be achieved, for example, using ABI 431A Peptide Synthesizer (Perkin Elmer) in accordance with the instructions provided by the manufacturer. Additionally, the amino acid sequence of atlastin, or any part thereof, may be altered during direct synthesis and/or combined using chemical methods with other sequences to produce a variant polypeptide.

III. Detection of Atlastin Alleles

A. Atlastin Alleles

In some embodiments, the present invention includes alleles of atlastin that correlate to susceptibility to HSP (e.g., including, but not limited to, the mutations shown in SEQ ID NOS: 3, 4 and 5). Analysis of naturally occurring human atlastin alleles revealed that patients with increased susceptibility to HSP have a mutant atlastin allele.

The present invention is not limited to a particular mechanism of action. Indeed, an understanding of the mechanism of action is not necessary to practice the present invention. Nevertheless, it is contemplated that atlastin is involved in normal GTPase signalling. It is contemplated that in HSP reduced function or nonfunctional atlastin result in reduced neuronal signalling and is the direct mechanism for responsible for HSP.

However, the present invention is not limited to the mutations described in the application. Any mutation that results in the undesired phenotype (e.g., an altered level of atlastin GTPase activity, or the presence of or susceptibility to HSP) is within the scope of the present invention. For example, in some embodiments, the present invention provides alleles containing one or more single-nucleotide changes of atlastin.

B. Detection of Variant Alleles

Accordingly, the present invention provides methods for determining whether a patient has a variant atlastin allele that will lead to HSP. In other embodiments, the present invention provides methods for providing a prognosis of increased risk for HSP disease to an individual based on the presence or absence of one or more variant alleles of atlastin. In preferred embodiments, the variation is a mutation resulting in decreased levels of atlastin or reduced functionality of atlastin.

A number of methods are available for analysis of variant (e.g., mutant or polymorphic) nucleic acid sequences. Assays for detections polymorphisms or mutations fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

1. Direct Sequencing Assays

In some embodiments of the present invention, variant sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNP or mutation of interest) is sequenced using any suitable method, including but not limited to manual sequencing using radioactive marker nucleotides, or automated sequencing. The results of the sequencing are displayed using any suitable method. The sequence is examined and the presence or absence of a given SNP or mutation is determined.

2. PCR Assays

In some embodiments of the present invention, variant sequences are detected using a PCR-based assay. In some embodiments, the PCR assay comprises the use of oligonucleotide primers that hybridize only to the variant or wild type allele of atlastin (e.g., to the region of polymorphism or mutation). Both sets of primers are used to amplify a sample of DNA. If only the mutant primers result in a PCR product, then the patient has the mutant atlastin allele. If only the wild-type primers result in a PCR product, then the patient has the wild type allele of atlastin.

3. Fragment Length Polymorphism Assays

In some embodiments of the present invention, variant sequences are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I [Third Wave Technologies, Madison, Wis.] enzyme). DNA fragments from a sample containing a SNP or a mutation will have a different banding pattern than wild type.

a. RFLP Assays

In some embodiments of the present invention, variant sequences are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

b. CFLP Assays

In other embodiments, variant sequences are detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888,780; each of which is herein incorporated by reference). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

4. Hybridization Assays

In preferred embodiments of the present invention, variant sequences are detected a hybridization assay. In a hybridization assay, the presence of absence of a given SNP or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.) (1991) Current Protocols in Molecular Biology, John Wiley & Sons, NY). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the SNP or mutation being detected is allowed to contact the membrane under a condition or low, medium, or high stringency conditions. Unbound probe is removed and the presence of binding is detected by visualizing the labeled probe.

b. Detection of Hybridization Using "DNA Chip" Assays

In some embodiments of the present invention, variant sequences are detected using a DNA chip hybridization assay.

In this assay, a series of oligonucleotide probes are affixed to a solid support. The oligonucleotide probes are designed to be unique to a given SNP or mutation. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip". Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. A laser-based fluorescence scanner is used to detect binding.

In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the amidite A is delivered only to the sites where amidite A is to be coupled during that synthesis step and so on. Common reagents and washes are delivered by flooding the entire surface and then removing them by spinning.

DNA probes unique for the SNP or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments of the present invention, hybridization is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified genomic DNA. The isolated DNA sample is contacted with the first probe specific either for a SNP/mutation or wild type sequence and allowed to hybridize. Then a secondary probe, specific to the first probe, and containing the fluorescein label, is hybridized and the enzyme is added. Binding is detected by using a fluorescent plate reader and comparing the signal of the test sample to known positive and negative controls.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin).

5. Mass Spectroscopy Assays

In some embodiments, a MassARRAY system (Sequenom, San Diego, Calif.) is used to detect variant sequences (See e.g., U.S. Pat. Nos. 6,043,031; 5,777,324; and 5,605,798; each of which is herein incorporated by reference). DNA is isolated from blood samples using standard procedures. Next, specific DNA regions containing the mutation or SNP of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization-Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged, when an electrical field pulse is subsequently applied to the tube the diagnostic product is launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3-5 second including repetitive data collection. The SpectroTYPER software then calculates, records, compares and reports the genotypes at the rate of three seconds per sample.

6. Variant Analysis by Differential Antibody Binding

In other embodiments of the present invention, antibodies (See below for antibody production) are used to determine if an individual contains an allele encoding an atlastin gene containing a mutation. In preferred embodiments, antibodies are utilized that discriminate between mutant (i.e., truncated proteins); and wild-type proteins (SEQ ID NO:2).

7. Kits for Analyzing Risk of HSP

The present invention also provides kits for determining whether an individual contains a wild-type or variant (e.g., mutant or polymorphic) allele of atlastin. In some embodiments, the kits are useful determining whether the subject is at risk of developing HSP. The diagnostic kits are produced in a variety of ways. In some embodiments, the kits contain at least one reagent for specifically detecting a mutant atlastin allele or protein. In some preferred embodiments, the kits contain reagents for detecting a SNP caused by a single nucleotide substitution of the wild-type gene. In these preferred embodiments, the reagent is a nucleic acid that hybridizes to nucleic acids containing the SNP and that does not bind to nucleic acids that do not contain the SNP. In other preferred embodiments, the reagents are primers for amplifying the region of DNA containing the SNP. In still other embodiments, the reagents are antibodies that preferentially bind either the wild-type or mutant atlastin proteins. In some embodiments, the kit contains instructions for determining whether the subject is at risk for developing HSP. In preferred embodiments, the instructions specify that risk for developing HSP is determined by detecting the presence or absence of a mutant atlastin allele in the subject, wherein subjects having an allele containing a single nucleotide substitution mutation have an increased risk of developing HSP. In some embodiments, the kits include ancillary reagents such as buffering agents, nucleic acid stabilizing reagents, protein stabilizing reagents, and signal producing systems (e.g., florescence generating systems as Fret systems). The test kit may be packages in any suitable manner, typically with the elements in a single container or various containers as necessary along with a sheet of instructions for carrying out the test. In some embodiments, the kits also preferably include a positive control sample.

8. Bioinformatics

In some embodiments, the present invention provides methods of determining an individual's risk of developing HSP based on the presence of one or more variant alleles of atlastin. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of contacting HSP associated with a given polymorphism, as well as the sequences). Results are then delivered to the user (e.g., via one of the computers or via the internet).

IV. Generation of Atlastin Antibodies

Antibodies can be generated to allow for the detection of atlastin protein. The antibodies may be prepared using various immunogens. In one embodiment, the immunogen is anatlastin peptide to generate antibodies that recognize human atlastin. Such antibodies include, but are not limited to polyclonal, monoclonal, chimeric, single chain, Fab fragments, and Fab expression libraries.

Various procedures known in the art may be used for the production of polyclonal antibodies directed against atlastin. For the production of antibody, various host animals can be immunized by injection with the peptide corresponding to the atlastin epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward atlastin, it is contemplated that any technique that provides for the production of antibody molecules by continuous cell lines in culture will find use with the present invention (See e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein (1975) Nature 256:495-497), as well as the trioma technique, the human B-cell hybridoma technique (See e.g., Kozbor et al. (1983) Immunol. Tod., 4:72), and the EBV-hybridoma technique to produce human monoclonal antibodies (Cole et al. (1985) in *Monoclonal Antibodies and Cancer Therapy*, Alan R. Liss, Inc., pp. 77-96). In an additional embodiment of the invention, monoclonal antibodies are produced in germ-free animals utilizing technology such as that described in PCT/US90/02545). Furthermore, it is contemplated that human antibodies will be generated by human hybridomas (Cote et al. (1983) Proc. Natl. Acad. Sci. USA 80:2026-2030) or by transforming human B cells with EBV virus in vitro (Cole et al. (1985) in *Monoclonal Antibodies and Cancer Therapy*, Alan R. Liss, pp. 77-96).

In addition, it is contemplated that techniques described for the production of single chain antibodies (U.S. Pat. No. 4,946,778; herein incorporated by reference) will find use in producing atlastin specific single chain antibodies. An additional embodiment of the invention utilizes the techniques described for the construction of Fab expression libraries (Huse et al. (1989) Science 246:1275-1281) to allow rapid and easy identification of monoclonal Fab fragments with the desired specificity for atlastin.

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of atlastin (e.g., for Western blotting), measuring levels thereof in appropriate biological samples, etc. The antibodies can be used to detect atlastin in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of atlastin using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of atlastin detected by immunoblotting (Western blotting). Immunoblotting techniques are generally more effective with antibodies generated against a peptide corresponding to an epitope of a protein, and hence, are particularly suited to the present invention.

In other embodiments, the antigen is a peptide fragment of atlastin; preferably, the fragment is of high antigenicity. In yet other embodiment, the immunogen is a variant or mutant of atlastin peptide to generate antibodies that recognize the variant or mutant atlastin. Such antibodies include, but are not limited to polyclonal, monoclonal, chimeric, single chain, Fab fragments, and Fab expression libraries, and are prepared and used as described above. These antibodies can then be used to detect the presence of a fragment or variant or mutant atlastin in a biological sample from an individual, as described above, and thus to predict the susceptibility of the individual to HSP.

For example, peptide antibodies may be synthesized against peptide in any one of the exons. Additionally, peptide fragments may be selected on the basis of determinations by computer algorithms and other methods as having high "antigenicity" (likely to elicit an immune response); the selected peptides were then synthesized. The peptide fragments are injected into rabbits, and the rabbits periodically bled and boosted with the peptide antigen between bleeds. This serum is used as the source of the antibodies, while the serum before peptide injection is used as a negative control. The antibodies are affinity purified by passing the serum over a column composed of the peptide to purify only antibodies that bind the peptide. At least one of these antibodies in the unpurified state detects a protein of approximately the right size that is present in normal plasma but not patient plasma. Antibodies are also prepared against other peptide fragments.

V. Methods of Treatment of HSP

A. Gene Therapy Using Atlastin

The present invention also provides methods and compositions suitable for gene therapy to alter atlastin expression, production, or function. As described above, the present invention provides atlastin genes and provides methods of obtaining atlastin genes from different species. Thus, the methods described below are generally applicable across many species. In some embodiments, it is contemplated that the gene therapy is performed by providing a subject with a wild-type allele of atlastin (i.e., an allele that does not contain a mutation). Subjects in need of such therapy are identified by the methods described above.

Viral vectors commonly used for in vivo or ex vivo targeting and therapy procedures are DNA-based vectors and retroviral vectors. Methods for constructing and using viral vectors are known in the art (See e.g. (1992) Miller and Rosman, BioTech., 7:980-990). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al. (1991) Mol. Cell. Neurosci., 2:320-330), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 (1992); See also, La Salle et al. (1993) Science 259:988-990); and a defective adeno-associated virus vector (Samulski et al. (1987) J. Virol., 61:3096-3101; Samulski et al. (1989) J. Virol., 63:3822-3828; and Lebkowski et al. (1988) Mol. Cell. Biol., 8:3988-3996).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-_), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. The present invention contemplates adenoviruses of both human and animal origin. (See e.g., WO94/26914). Various serotypes of adenovirus exist. Those adenoviruses of animal origin that can be used within the scope of the present invention include adenoviruses of canine, bovine, murine (e.g., Mav1, Beard et al. (1990) Virol., 75-81), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO95/02697), the E2 region (e.g., WO94/28938), the E4 region (e.g., WO94/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al. (1991) Gene 101:195; EP 185 573; and Graham (1984) EMBO J., 3:2917). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al. (1977) J. Gen. Virol., 36:59), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No. 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al. (1983) Cell 33:153; Markowitz et al. (1988) J. Virol., 62:1120; PCT/US95/14575; EP 453242; EP178220; Bernstein et al. (1985) Genet. Eng., 7:235; McCormick, (1985) BioTechnol., 3:689; WO 95/07358; and Kuo et al., (1993):845). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al. (1987) Virol., 61:1639). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al. (1987) Proc. Natl. Acad. Sci. USA 84:7413-7417; See also, Mackey, et al. (1988) Proc. Natl. Acad. Sci. USA 85:8027-8031; Ulmer et al. (1993) Science 259:1745-1748). The use of cationic lipids may promote encapsulation of negatively charged nucleic acids, and also promote fusion with negatively charged cell membranes (Felgner and Ringold (1989) Science 337:387-388). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al. (1992) J. Biol. Chem., 267:963; Wu and Wu (1988) J. Biol. Chem., 263:14621; and Williams et al. (1991) Proc. Natl. Acad. Sci. USA 88:2726). Receptor-mediated DNA delivery approaches can also be used (Curiel et al. (1992) Hum. Gene Ther., 3:147; and Wu and Wu (1987) J. Biol. Chem., 262:4429).

B. Administration of Atlastin Polypeptides

The present invention also provides methods and compositions suitable for administering atlastin to a patient suffering from HSP. As described above, the present invention provides nucleotides encoding atlastin and fragments, mutants, variants, and fusions thereof, and methods of producing the encoded polypeptides. The methods described below are generally applicable across many species.

In some embodiments, the invention provides a composition comprising purified atlastin peptides; in other embodiments, the invention provides a composition comprising purified atlastin polypeptide fragments, mutants, variants, or fusions, all of which possess the biological activity of atlastin. Fragments, mutants, variants, or fusions may be used as necessary to alter characteristics of atlastin to improve its performance as a therapeutic treatment of HSP. Such characteristics include stability during storage and administration, circulating half-life, levels of activity, substrate specificity, localization to a particular tissue, and interaction with other molecules, such as receptors or enzymatic complexes. For example, the protein is preferably engineered to have a very long circulating half life. Such characteristics can be introduced as described above. The polypeptides can be produced as described above. The compositions are formulated as described.

In other embodiments, the invention provides a method of treating a patient with HSP, which comprises administering a therapeutically effective amount of atlastin such that symptoms of the disease are alleviated. As is well known in the medical arts, dosages for any one patient depends upon many factors, including the patient's size, body surface area, age, the particular compound to be administered, sex, time and route of administration, general health, and interaction with other drugs being concurrently administered. Although any method of administration is anticipated, as described further below, preferably the polypeptide is administered intravenously.

VI. Drug Screening Using Atlastin

The present invention provides methods and compositions for using atlastin as a target for screening drugs that can alter, for example, atlastin GTPase activity and associated symptoms (e.g., HSP). For example, drugs that induce or inhibit atlastin GTPase activity can be identified by screening for compounds that target atlastin or regulate atlastin gene expression. The present invention is not limited to a particular mechanism of action. Indeed, an understanding of the mechanism of action is not necessary to practice the present invention.

In one screening method, candidate compounds are evaluated for their ability to alter atlastin GTPase activity by adding the compound in the presence of atlastin to an assay for the atlastin GTPase activity and determining the effects of the compound on the level of GTPase activity.

Another technique uses atlastin antibodies, generated as discussed above. Such antibodies capable of specifically binding to atlastin peptides can be used to detect the presence of any peptide that shares one or more antigenic determinants of the atlastin peptide. Such peptides can then be evaluated for protease activity as described above.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with atlastin and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in reporter gene assays that monitor cellular responses at the transcription/translation level. In still further embodiments, the cells can be used in cell proliferation assays to monitor the overall growth/no growth response of cells to external stimuli.

The cells are useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminescent products of specific substrates (e.g., X-gal and luciferin). Comparisons between compounds of known and unknown activities may be conducted as described above.

VII. Pharmaceutical Compositions Containing Atlastin Nucleotides, Peptides, and Antibodies, and Analogs The present invention further provides pharmaceutical compositions which may comprise all or portions of atlastin polynucleotide sequences, atlastin polypeptides, inhibitors or antagonists of atlastin bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by an increase or decreased atlastin GTPase activity. The invention provides methods for increasing atlastin GTPase activity by administering peptides or peptide fragments or variants of atlastin. Alternatively, drugs which act to increase atlastin GTPase activity as discovered through screening methods described above, are administered.

Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, atlastin nucleotides and atlastin amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, atlastin polynucleotide sequences or atlastin amino acid sequences may be administered alone to individuals subject to or suffering from HSP.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of atlastin may be that amount that results in atlastin GTPase activity comparable to normal individuals who are not suffering from HSP. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of atlastin, conditions indicated on the label may include treatment of condition related to apoptosis.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts atlastin levels.

A therapeutically effective dose refers to that amount of atlastin or variant or drug that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. No. 4,657,760; 5,206,344; or 5,225,212, all of which are herein incorporated by reference). Those skilled in the art will employ different formulations for atlastin than for the inducers or enhancers of atlastin. Administration to the bone marrow may necessitate delivery in a manner different from intravenous injections.

VIII. Transgenic Animals Expressing Exogenous Atlastin Genes and Homologs, Mutants, and Variants Thereof The present invention contemplates the generation of transgenic animals comprising an exogenous atlastin gene or homologs, mutants, or variants thereof. In preferred embodiments, the transgenic animal displays an altered phenotype as compared to wild-type animals. In some embodiments, the altered phenotype is the overexpression of mRNA for a atlastin gene as compared to wild-type levels of atlastin expression. In other embodiments, the altered phenotype is the decreased expression of mRNA for an endogenous atlastin gene as compared to wild-type levels of endogenous atlastin expression. In other embodiments, the transgenic mice have a knock out mutation of the at/astin gene. In still further embodiments, the altered phenotype is expression of a atlastin mutant gene. In preferred embodiments, the transgenic animals display a HSP disease phenotype. Methods for analyzing the presence or absence of such altered phenotypes include Northern blotting, mRNA protection assays, RT-PCR, detection of protein expression with antibodies, and detection of atlastin GTPase activity.

The transgenic animals of the present invention find use in drug and treatment regime screens. In some embodiments, test compounds (e.g., a drug that is suspected of being useful to treat HSP) and control compounds (e.g., a placebo) are administered to the transgenic animals and the control animals and the effects evaluated. The effects of the test and control compounds on disease symptoms are then assessed.

The transgenic animals can be generated via a variety of methods. In some embodiments, embryonic cells at various developmental stages are used to introduce transgenes for the production of transgenic animals. Different methods are used depending on the stage of development of the embryonic cell. The zygote is the best target for micro-injection. In the mouse, the male pronucleus reaches the size of approximately 20 micrometers in diameter which allows reproducible injection of 1-2 picoliters (pl) of DNA solution. The use of zygotes as a target for gene transfer has a major advantage in that in most cases the injected DNA will be incorporated into the host genome before the first cleavage (Brinster et al. (1985) Proc. Natl. Acad. Sci. USA 82:4438-4442). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich (1976) Proc. Natl. Acad. Sci. USA 73:1260). Efficient infection of the blastomeres is obtained by enzymatic treatment to remove the zona pellucida (Hogan et al. (1986) in *Manipulating the Mouse Embryo*, Cold Spring Harbor Laboratory Press, Cold Spring Harbor, N.Y.). The viral vector system used to introduce the transgene is typically a replication-defective retrovirus carrying the transgene (Jahner et al. (1985) Proc. Natl. Acad. Sci. USA 82:6927). Transfection is easily and efficiently obtained by culturing the blastomeres on a monolayer of virus-producing cells (Van der Putten, supra; Stewart, et al. (1987) EMBO J., 6:383). Alternatively, infection can be performed at a later stage. Virus or virus-producing cells can be injected into the blastocoele (Jahner et al. (1982) Nature 298:623). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al. (1982) supra). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen (1995) Mol. Reprod. Dev., 40:386).

In other embodiments, the transgene is introduced into embryonic stem cells and the transfected stem cells are utilized to form an embryo. ES cells are obtained by culturing pre-implantation embryos in vitro under appropriate conditions (Evans et al. (1981) Nature 292:154; Bradley et al. (1984) Nature 309:255; Gossler et al. (1986) Proc. Acad. Sci. USA 83:9065; and Robertson et al. (1986) Nature 322:445). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoele of a blastocyst-stage embryo and contribute to the germ line of the resulting chimeric animal (for review, See, Jaenisch (1988) Science 240:1468). Prior to the introduction of transfected ES cells into the blastocoele, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoele.

In still other embodiments, homologous recombination is utilized knock-out gene function or create deletion mutants. Methods for homologous recombination are described in U.S. Pat. No. 5,614,396, incorporated herein by reference.

IX. Screens to Identify Atlastin Interactive Molecules

There are several different approaches contemplated by the present invention to look for small molecules that specifically bind atlastin and interact with atlastin. One approach is to transfect expression constructs comprising nucleic acid encoding atlastin into cells. Atlastin, along with any interactive molecules could then be precipitated and identified. Cells may be transiently transfected or stably transfected with the construct under control of an inducible promoter. Other embodiments would include translation of the invention and purification of the peptide. The purified peptide could then be used to test specific compound:protein interactions. Additionally, it is possible to generate antibodies to the translated invention allowing for the development of immunological assays such as, but not limited to, RIA, ELISA or Western blot. Furthermore, transgenic animals could be produced allowing for in vivo assays to be conducted.

A. In Vitro Assays a. Transfection Assays

Transfection assays allow for a great deal of flexibility in assay development. The wide range of commercially available transfection vectors will permit the expression of the atlastin gene of the present invention in a extensive number of cell types. In one embodiment, cells are transiently transfected with an expression construct comprising nucleic acid encoding atlastin that includes an inducible promotor allowing for the initiation of translation and transcription when needed. Cells would be exposed to the agent suspected of modulating atlastin expression and expression would be turned on and would be measured. Rates of atlastin expression in cells expressing the invention are compared to rates of expression in cells transfected with a construct expressing a mutant atlastin gene and cells expressing a control expression vector (e.g., an empty expression vector). Rates of expression can be quantitated by any of a number of ways reported in the literature and known to those practiced in the art.

In another embodiment, stably transfected cells lines are developed, i.e., cell lines stably expressing the atlastin mutants of the present invention. The use of an inducible promoter would be utilized in these systems. Screening assays for compounds suspected of modulating atlastin activity would be conducted in the same manner as with the transient transfection assays. Using stably transfected cell lines would allow for greater consistency between experiments and allow for inter-experimental comparisons.

B. In Vivo Assays a. Transgenic Animal Assays

In one embodiment transgenic animals will be constructed using standard protocols (see, for example, Sambrooke, et al.). The generation of transgenic animals will allow for the investigation of diseases for which the mutated forms of atlastin may provide the means for determining the physiology of the disease or its treatment.

2. Screen to Identify Tumors Expressing Similar or Homologous Gene Mutations

In one embodiment screens will be constructed using microassay microchip techniques. This will allow for the development of a high-through-put screen for the identification of cells expressing mutant genes similar to, or homologous with, the atlastin genes.

3. Screens to Identify Atlastin Signal Pathway Constituents

A. In Vitro Assays

There are several different approaches to identifying atlastin interactive molecules. The invention would allow the identification of proteins that may only associated with nonactive (or reduced activity) atlastin or constitutively active atlastin molecules. Such proteins may regulate atlastin function. Techniques that may be used are, but not limited to, immunoprecipitation of atlastin with antibodies generated to the transcription product of the invention. This would also bring down any associated bound proteins. Another method is to generate fusion proteins containing the mutant form of atlastin connected to a generally recognized pull-down protein such as glutathione S-transferase. Bound proteins can then be eluded and analyzed.

a. Immunoprecipitation

After the generation of antibodies to wild type and mutant atlastin, cells expressing transfected atlastin are lysed and then incubated with one of the antibodies. Antibodies with the bound atlastin and any associated proteins can then be pulled down with protein-A Sepharose or protein-G Sepharose beads, using standard techniques.

b. Fusion Protein Pull-Down

A method similar to immunoprecipitation is to construct fusion proteins of the mutant and wild type atlastin and glutathione S-transferase (GST). The atlastin fusion proteins are then incubated with cell extracts and then removed with glutathione Sepharose beads. Any bound, atlastin proteins are then characterized.

B. In Vivo Assays a. Yeast Two-Hybrid System

The yeast two-hybrid system that identifies the interaction between two proteins by reconstructing active transcription factor dimers. The dimers are formed between two fusion proteins, one of which contains a DNA-binding domain (DB) fused to the first protein of interest (DB-X) and the other, an activation domain (AD) fused to the second protein of interest (AD-Y). The DB-X:AD-Y interaction reconstitutes a functional transcription factor that activates chromosomally-integrated reporter genes driven by promoters containing the relevant DB binding sites. Large cDNA libraries can be easily screened with the yeast-two hybrid system. Yeast cDNA libraries are commercially available. Standard molecular biological techniques can be employed to isolate and characterize the interacting protein.

Screens to Identify Atlastin Homologs

Standard molecular biological techniques can be used to identify atlastin homologs in humans or other species. For example, the present invention contemplates a variety of approaches including, but are not limited to, DNA-DNA hybridization techniques (e.g., Southern blots) and DNA-RNA hybridization techniques (e.g., Northern blots). Additional techniques may include, for example, immunoscreening of proteins made from library stocks with antibodies generated to translation products of atlastin. Furthermore, immunoprecipitation of known or suspected interactive proteins of atlastin can be followed by the identification of possible mutant atlastin homologs with antibodies generated to translation products of atlastin.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); L (liters); ml (milliliters); μl (microliters); cm (centimeters); mm (millimeters); μm (micrometers); nm (nanometers); ° C. (degrees Centigrade); RDA (representational difference analysis); nts (nucleotides); n (number); gDNA (genomic DNA); cM (centimorgans).

Example 1

Genetic linkage analysis. This example shows how individuals were selected and how genetic analysis was performed. Three autosomal dominant HSP kindreds were evaluated. HSP was diagnosed according to published criteria (Fink, et al., 1996). Each affected subject had symptom onset before age 10 years (usually before age 5). Prenatal diagnosis of HSP and skeletal muscle biopsy in ADHSP-T kindred have been reported previously for these individuals. Samples were obtained from 111 control subjects who were older than age 60, examined by a team of Neurology and Psychiatry resident physicians, and had completed the Screening Criteria of Informative Diagnoses. This study and the process of informed consent were approved by the University of Michigan Institutional Review Board.

DNA was extracted from peripheral blood leukocytes, microsatellite DNA polymorphisms analyzed, and two-point lodscores were calculated. For genetic linkage analysis, we used an autosomal dominant monogenic mode of inheritance, assumed disease allele frequency of 0.001, and assigned genetic penetrance=0.90. There were too few marrying-in spouses to calculate allele frequencies accurately. Instead, allele frequencies were assumed to be equal.

Genetic linkage to the SPG3 locus was assessed by examination of markers D14S976, D14S306, D14S1031, D14S301. In addition, for the ADHSP-S kindred, linkage to the SPG3 locus was assessed to a highly polymorphic trinucleotide repeat $(CTT)_{55}$ present in BAC 476J6 of contig NT_010050. PCR primers GAG1a (5'-acttcagcctaggcgacagag-3' [SEQ ID NO:6], NT_010050 nucleotides 807918 through 807938); and GAG1b (5'-aatggtagaagcttaaatt-3' [SEQ ID NO:7], NT_010050 nucleotides 807700 through 807718) were used for this analysis.

Two-point lodscores showed that the disorder in each kindred was linked to the SPG3 locus. Maximum two-point lodscores (at θ=0) were +5.59 for D14S584 in ADHSP-T; +4.63 for D14S746 in ADHSP-P; and +2.28 for D14S269 and +2.70 for GAG1 in ADHSP-S.

Analysis of linkage to additional loci for autosomal dominant HSP was assessed by examination of linkage to SPG4 (D2S352, D2S367, D2S2325, D2S2203, D2S2351), SPG6 (D15S118, D15S542, D15S543, D15S128), SPG8 (D8S266, D8S1799, D8S1138, D8S1179), SPG11 (D12S83, D12S1691, D12S368), SPG12 (D19S412, D19S420, D19S408, D19S881), SPG13 (D2S2318, D2S2392). Significantly, negative lodscores excluded these other HSP loci in each family.

Example 2

Identification of SPG3 candidate genes. DNA sequences of the Genoscope contig and the NCBI contigs spanning the SGP3 locus (D14S259 to D14S978) are available in publicly accessible databases (The National Center for Biological Information and Genescope [sponsored by The French Ministery of Education, Research and Technology (MENRT); The French Agency of Scientific Research (CNRS) and The French Scientific Innovation and Transfer Company (FIST)]). Some ESTs and cDNA sequences were listed with each annotated NCBI contig; others were identified by analysis of these contig DNA sequences with GENESCAN and GRAIL programs of the PIPELINE suite of programs (from the Computational Biology Section of the Life Sciences Division of Oak Ridge National Laboratory, Oak Ridge, Tenn.). Potential exonic sequences and candidate genes identified in this manner were compared through BLAST analysis to sequences in public databases (The National Center for Biological Information, Genbank and The National Center for Biological Information, Human Genome Sequencing). Intron-exon boundaries for these potential candidate genes were determined, whenever possible, by comparing gDNA sequences with ESTs (The National Center for Biological Information, Expressed Sequence Tags database). Grail and Genescan programs were used to predict intron-exon boundaries for putative genes for which EST and cDNA clones were not available. Intronic primers were designed (using the Primerselect LaserGene program from DNAStar) to amplify each candidate gene exon.

The SPG3 locus extends 2.7 cM between D14S259 and D14S978, an interval spanned by a BAC contig beginning with BAC R-586C14 (Genescope [sponsored by The French Ministery of Education, Research and Technology (MENRT); The French Agency of Scientific Research (CNRS) and The French Scientific Innovation and Transfer Company (FIST)]); and by 12 BAC contigs listed in Genbank (data not shown). We confirmed the STS content of these contigs by a combination of STS amplification from individual BAC elements; and by "virtual" PCR (using BLAST analysis to determine if DNA sequences of given STSs were contained in the annotated contig sequence (The National Center for Biological Information). Twenty-three potential candidate genes were identified in these contigs by analysis of ESTs and cDNA sequences listed with annotated NCBI contigs; and by PIPELINE analysis of contig and individual BAC DNA sequences (from the Computational Biology Section of the Life Sciences Division of Oak Ridge National Laboratory, Oak Ridge, Tenn.). Thirteen of these candidate genes were analyzed.

Example 3

Sequencing of SPG3 candidate genes. Initial analysis of candidate genes for disease-specific mutations was performed in gDNA samples from three affected and one unaffected subject from ADHSP-P kindred. Following the discovery of atlastin gene mutations in affected subjects in this initial test cohort, we analyzed gDNA samples from each available subject from this kindred and from ADHSP-T and ADHSP-S kindreds and 111 control subjects. 50 ng of DNA was used in PCR amplification of each candidate gene exon (see Table 1).

PCR products were purified through Sephadex G-50 columns and analyzed by agarose gel electrophoresis before cycle sequencing. Purified PCR products were sequenced with one of the PCR primers according to the manufacturer's instruction using the ABI PRISM dRhodamine Terminator Cycle Sequencing Ready Reaction Kit (PE Applied Biosystems, USA) on an ABI PRISM 3100 Genetic Analyzer. Both strands of each exon were sequenced. Sequence data was analyzed with SeqMan of Lasergene programs (DNAStar).

Reverse-transcription PCR (RT-PCR) was performed with total RNA (1 µg) from human adult and fetal brain and adult lung, kidney, heart, and liver (purchased from Stratagene, USA) using an RT-PCR kit (Gibco/BRL, USA) following the supplier's instructions. Following reverse transcription (50° C. for 30 min), single-stranded cDNA was PCR amplified (20 cycles of 94° C. for 30 sec, 55° C. for 30 sec, and 72° C. for 30 sec) using primers:

```
forward
5'-CAGGGAACCAGCATGAAGAACTA-3'    (SEQ ID NO: 8)

reverse:
5'-CCCCGGCAGGTGATTTTATT-3'       (SEQ ID NO: 9)
``` that amplify a 244 bp DNA fragment spanning from 886 to 1130 of atlastin cDNA. RT-PCR products were visualized through agarose gel electrophoresis, and compared to molecular size standards.

Quantitative analysis of atlastin expression in multiple human tissues was assessed in total RNA samples from human adult lung, kidney, heart, liver (purchased from Stratagene, USA) and brain (purchased from Gibco/BRL, USA) by quantitative RT-PCR using the LightCycler-RNA Amplification Kit SYBR Green I Kit (Roche, USA) according to the manufacturer's instructions. LightCycler programs included a reverse transcription step (55° C. for 10 min), an initial denaturing (95° C. for 30 sec) followed by 45 cycles of 95° C. for 1 sec, 56° C. for 10 sec, and 72° C. for 12 seconds. Final melting curve analysis was performed immediately after the cycling process according to manufacturer☐s directions. Atlastin gene expression measured in this way was normalized to L32 and _-actin gene expression so that comparisons could be made between these tissues.

This analysis revealed LOC51062 (Genbank accession number: NM-015915), a hypothetical cDNA identical to a portion of I.M.A.G.E. consortium cDNA clone 25221 (Genbank accession number AF131801), but which contains an additional 14 bp at the 5'end and 60 bp of additional 3' untranslated sequence. Analysis of LOC51062/25221 exonic sequences in ADHSP-P subjects revealed heterozygosity (both C and A) at nucleotide 541 of cDNA 25221 (corresponding to nucleotide 944 in the full length cDNA, FIGS. 2A and 2B) in each affected subject (n=13); whereas each unaffected subject (n=6) and each control subject (n=111) had only C at this position which agreed with the gDNA sequence of contig NT_010035 and cDNA sequence of LOC51062 and 25221. Sequencing this region in samples from another SPG3-linked ADHSP kindred (ADHSP-T) revealed heterozygosity (A and G; FIGS. 2A and 2B) at cDNA 25221 nucleotide 538 (corresponding to nucleotide position 941 in the full length cDNA, FIGS. 2A and 2B) in each affected subject (n=16); each unaffected subject (n=22) in this kindred and each control subject (n=111) had only A, identical to gDNA sequence of contig NT_010035 and cDNA sequence of LOC51062 and 25221. Sequencing each remaining LOC51062/25221 exon in three affected and one unaffected subject from ADHSP-P and ADHSP-T kindreds did not reveal any other disease specific mutation. However, sequencing each LOC51062/25221 exon in a samples from a third SPG3-linked ADHSP kindred (ADHSP-S) revealed heterozygosity (C and T) at nucleotide position 883 (of the full length cDNA, discussed below) in each affected subject (n=8); while each unaffected subject (n=2) in this kindred and each control subject (n=111) had only C at this position. Sequencing each remaining exon in affected and unaffected subjects in this kindred did not reveal any other disease-specific mutations.

TABLE 1

| Exon | Primer | Primer sequence | PCR product (bp) | PCR condition * |
|---|---|---|---|---|
| 1 | 1f | CCCTTGGCCCTCCCTGTCT (SEQ ID NO: 13) | 454 | C |
|  | 1r | GGGGGTGCTGTTTATTTGTTT (SEQ ID NO: 14) |  |  |
| 2 | 2f | GTCCCCAAAGCACTGAGGTT (SEQ ID NO: 15) | 465 | C |
|  | 2r | CTTGGCACTTTGAGATGATTAGC (SEQ ID NO: 16) |  |  |
|  | 2.1f | GAAAATTGGTCTGTGTAGTT (SEQ ID NO: 17) | 401 | C |
|  | 2.1r | AAGAGGAGGAGCCAGTGAAAA (SEQ ID NO: 18) |  |  |
| 3 | 3f | GTTATAATTTCGCCTACTCTGA (SEQ ID NO: 19) | 500 | B |
|  | 3r | GATGGTTGCTCCTCTGT (SEQ ID NO: 20) |  |  |
| 4 | 4f | TTCTAACCAAAGCAGTCA (SEQ ID NO: 21) | 464 | B |
|  | 4r | ATGGCATGTGTAAGAAAT (SEQ ID NO: 22) |  |  |
| 5 | 5f | TGGGCCAATAGTTCCTGTT (SEQ ID NO: 23) | 370 | A |
|  | 5r | TCATTGTTCATTCCTTATTGTCTC (SEQ ID NO: 24) |  |  |

TABLE 1-continued

| Exon | Primer | Primer sequence | PCR product (bp) | PCR condition * |
|---|---|---|---|---|
| 6 | 6f | TTCCTCATTTCCATCTCATTCTAT (SEQ ID NO: 25) | 295 | A |
|   | 6r | TTGCAGGTGCTAAAGTTCTCT (SEQ ID NO: 26) | | |
| 7 | 7f | CACCAAATGATCCAACAGA (SEQ ID NO: 27) | 208 | A |
|   | 7r | GGCACCTTAAAGTCCTCATA (SEQ ID NO: 28) | | |
| 8 | 8f | ATACATCCAGCGCCCATAGAATC (SEQ ID NO: 29) | 468 | A |
|   | 8r | TTAGTAGCAGCCCTGTCGTGTCAT (SEQ ID NO: 30) | | |
| 9 | 9f | CTCAAGATAAAAGGGGACAATAAT (SEQ ID NO: 31) | 465 | B |
|   | 9r | GGGAGGAAATGGGGGAGAT (SEQ ID NO: 32) | | |
| 10 | 10f | TGAACACATAAATAGGTAAAGT (SEQ ID NO: 33) | 416 | B |
|   | 10r | CAGATTGGCAGACAGAGATG (SEQ ID NO: 34) | | |
| 11 | 11f | GTTGCATGAAGGATACTGGTTT (SEQ ID NO: 35) | 254 | A |
|   | 11r | AATTATTTTGAGGACTTTGGTTTC (SEQ ID NO: 36) | | |
| 12 | 12f | GTGTGCTGAATTTAGTTG (SEQ ID NO: 37) | 626 | C |
|   | 12r | GATAGGGGTGGAAAGAT (SEQ ID NO: 38) | | |
| 13 | 13f | TTCTACACATTCATGAAACAAATACTG (SEQ ID NO: 39) | 607 | C |
|   | 13r | CACAATGGGGAATGAATGAAG (SEQ ID NO: 40) | | |
| 14 | 14f | TTTATAACAGCATTTTTGAAG (SEQ ID NO: 41) | 530 | B |
|   | 14r | ACACATTGAGGAGTTGAA (SEQ ID NO: 42) | | |

*PCR condition used included a initial denaturing at 94 C. for 5 min, then 30 cycles of 94° C. for 30 sec, 55° C. for 30 sec, and 72° C. for 30 sec. A final extension was performed at 72° C. for 7 min.
A: AmpTaq from Perkin Elmer was used. A total volume of 25 microliters include DNA (50 ng), 0.5 µM of primers, 200 µM of dNTPs, 1 U of AmpliTaq, 1.5 mM MgCl2, 10 mM Tris-HCl, pH 8.3, 50 mM KCl, and 0.01% (w/v) gelatin.
B: ExTaq from Kakara (Japan) was used. The 25 µl of PCR mix contained 50 ng DNA, 0.5 µM of primers, 25 mM TAPS (pH 9.3 at 25° C.), 50 mM KCl, 2 mM MgCl2, 1 mM 2-mercaptoethanol, and 200 µM dNTPs.
C. PCR reaction mix was the same as in A, but the PCR program used was 60-55° C. touchdown as follows: the annealing temperature in the first five cycles decreased by 1° C. every cycle from 60° C. to 55° C., followed by 30 cycles with an annealing temperature of 55° C.

Example 4

Obtaining full-length cDNA. I.M.A.G.E. consortium cDNA clone 25221 is contained in BAC 184B9 of annotated contig NT_010035. PIPELINE analysis of BAC 184B9 predicted additional transcribed sequences upstream of those in cDNA clone 25221. PCR amplification and sequence analysis of this upstream sequence from human fetal brain cDNA library (Strategene, U.S.A.) confirmed that this additional sequence was transcribed (data not shown) and was directly contiguous with the sequence of cDNA 25221. Comparison of this cDNA sequence with gDNA sequence of contig NT_010035 identified a conserved splice acceptor motif indicating the presence of additional 5' transcribed sequences. This was also suggested by Northern blot analysis (discussed below) in which a probe, created by amplifying nucleotides 886 to 1130 bp (full-length cDNA numbering) revealed a dominant 2.2 kb transcript, approximately 200 bp larger than available cDNA sequence (cDNA clone 25221 plus 200 bp of additional upstream contiguous sequence identified by PIPELINE analysis of BAC 184B9 and PCR and sequencing described above). We cloned and sequenced this additional upstream transcribed sequence by performing 5' RACE.

5' RACE was used (GeneRacer Kit, Invitrogen, Carlsbad, Calif., USA) to identify atlastin cDNA's 5' end. Human fetal brain RNA (1 µg) (purchased from Stratagene, USA) and atlastin-specific primer (5'-CTCGTTCAGATCCACCTC-3' [SEQ ID NO:10]) was used for first strand synthesis according to manufacturer's instruction; two nested gene-specific primers (5'-CCTTTTTCACTGGCTCCTCTCTTCTG-3' [SEQ ID NO:11], 5'-CTCCAGCAACAGATACAGCAA-CAACCTCCTT-3' [SEQ ID NO:12]) were then used to amplify and sequence the 5' end fragment of atlastin cDNA. (using GeneRacer Advanced RACE kit, Invitrogen, USA) with primers made to the 5' end of the additional cDNA sequence identified in BAC 184B9.

The 5' end of cDNA clone 25221 was extended 202 bp by 5' RACE. The resulting 2.2 kb cDNA sequence closely agreed with Northern blot analysis that revealed a 2.2 kb transcript primarily in adult and fetal brain. Northern blots were performed as follows: Human multiple tissue Northern blots (Human 12-Lane MTN Blot, Human Brain MTN Blot II, and Human Fetal MTN Blot II; Clontech, USA) were hybridized to $^{32}$P-labeled 244 bp probe created by PCR amplification of atlastin cDNA fragment between nucleotides 886 to 1130 of the atlastin cDNA. Northern blots were washed in SSC and 0.1% SDS at room temperature for 20 min and then 0.1×SSC and 0.1% SDS at 65° C. twice for 30 minutes. Images were developed on a Storm 840 phosphorimager (Molecular Dynamics) and exposed to x-ray film. A minor, slightly larger transcript (~2.7 kb) was also detected that could represent alternative splicing or cross-hybridization to an homologous transcript. Uniform mRNA abundance and splicing pattern were observed in different brain regions. Quantitative RT-PCR experiments indicated measurable expression in all tissues examined although expression in adult brain was at least 50-fold higher than in other tissues (data not shown).

The full-length cDNA and amino acid sequences (Genbank AY032844) of this novel gene (designated "atlastin") are shown (FIGS. 2A and 2B). Translating atlastin's 2.2 kb cDNA sequence revealed an initial methionine, followed by a single open reading frame of 558 amino acids and a stop codon. Comparing gDNA and cDNA sequences indicated that atlastin's coding sequence is divided into 14 exons that span ~69 kb. Consensus splice donor and splice acceptor sequences were identified for each exon. (data not shown).

Disease-specific atlastin mutations in ADHSP-P and ADHSP-T kindreds (atlastin cDNA nucleotides 944 and 941, respectively; FIGS. 2A and 2B) occur in atlastin exon 8 and are predicted to alter adjacent amino acids S259Y and H258R. Disease specific missense mutation (R239C) in ADHSP-S kindred occurs in exon 7 (atlastin cDNA nucleotide 883, FIGS. 2A and 2B).

Example 5

Determining atlastin's genomic organization and peptide analysis. Comparison between contig NT_010035 sequence and cDNA clone 25221 sequence identified 10 complete exons (numbers 3 through 11 and 14) and two partial exons (numbers 2 and 12). We identified exon 1 and the complete exon 2, the complete exon 12 and an additional, 15 bp exon (exon 13) by PIPELINE analysis and 5' RACE experiments (described above) and confirmed these exons by sequencing (see FIG. 1 and Table 2).

Atlastin homologues were found using multiple iterations of the default values of Psi-Blast. The secondary structure prediction was performed using the PHD prediction algorithm at the Predict Protein server.

The x-ray crystal structure of human guanylate binding protein 1 (hGBP1), PDB coordinate 1F5N, was used as a scaffold for the homology modeling of atlastin. The amino acid sequence alignment of hGBP1 and atlastin obtained from Psi-Blast was further optimized by hand. The optimized sequence alignment was imported to Modeller 4 (protein structure modelling software program from The Rockefeller University, New York, N.Y.) where the homology model was built and energy minimized. Several loop regions were removed and a subsequent energy minimization was performed in Modeller 4. The stereochemistry of the final homology model was analyzed using Procheck.

Example 6

Atlastin characterization. Following discovery of disease-specific atlastin mutations in three early-onset ADHSP kindreds linked to the SPG3 locus, we analyzed DNA samples from ten early onset ADHSP kindreds that were not preselected for linkage to the SPG3 locus. In two of these families, affected individuals had the same mutation (R239C) found in the ADHSP-S kindred. Subsequent genetic linkage analysis showed that the ADHSP-A kindred was linked to the SPG3 locus (maximum two point lodscore was +2.75 at θθ=0 for marker GAG1); ADHSP-M kindred was too small for meaningful genetic linkage analysis. Although kindreds with the R239C mutation are not apparently related, haplotype analysis has not excluded a distant founder effect.

Atlastin's amino acid sequence (m.w. 63.5 kD) contains three conserved motifs, P-loop (74GAFRKGKS81), DxxG (146DTQG), and RD (217RD) that characterize guanylate binding/GTPase active sites. Both DxxG and RD motifs are specific for a subset of GTPases including hGBP1, and mouse ARL-interacting protein-2 (accession number NP_062691) in which the GTPase active site includes an RD loop instead of an N/TKXD motif. We did not identify AAA motifs, present in spastin and paraplegin (mutations in which cause SPG4-linked ADHSP and SGP7-linked autosomal recessive HSP, respectively)

Atlastin shows significant homology to human guanylate binding protein 1 (hGBP1); as well as to guanylate binding proteins in mouse (ARL-interacting protein-2), *D. melanogaster* (CG6668 gene product), and *C. elegans* (putative guanylate binding protein AF303255). Human and murine members of the septin family of GTPases (human septin 3 [NP_061979] and mouse septin 3 [neuronal specific, NP_036019], also showed sequence similarity in the GTPase domain. No homology was observed to spastin, paraplegin, proteolipidprotein, or L1CAM, mutations in which cause other forms of HSP (and reviews).

Among these, atlastin shows greatest homology to hGBP1. Atlastin's predicted secondary structure includes an amino terminal GTPase domain followed by a predominantly helical domain, features that are parallel to those of hGBP1. Sequence homology between atlastin and hGBP1 was most pronounced throughout the length of the GTPase domain and halfway through the carboxy-terminal helical domain. Homology modeling of atlastin's GTPase domain and half of the helical domain predicted that atlastin has a tightly packed

TABLE 2

| Exon | Exon length (bp) | Exon start to end* | Intronic sequence at acceptor splice site | Intronic sequence at donor splice site | Intron* | Intron length (bp) |
|---|---|---|---|---|---|---|
| 1 | 202 | 126383-126584 | | GTGAGTAGCAAA TGAGAACT (SEQ ID NO: 43) | | |
| 2 | 248 | 101064-101311 | GTCACTGCTCT GTTCAACAG (SEQ ID NO: 44) | GTATGCAGGAAG TACTTTAA (SEQ ID NO: 45) | 101312-126379 | 25067 |
| 3 | 135 | 98067-98201 | TAGACTTTATC ATTTTATAG (SEQ ID NO: 46) | GTATGATGCTAA CTTCCTAA (SEQ ID NO: 47) | 98202-101063 | 2862 |
| 4 | 105 | 97503-97607 | TTTACTCTTCTT GCCTGTAG (SEQ ID NO: 48) | GTATGAAATAAG CCCATTTT (SEQ ID NO: 49) | 97608-98066 | 459 |
| 5 | 51 | 95241-95291 | AATTTTATTTCT TTATCAAG (SEQ ID NO: 50) | GTAACAATATTT ATTTTCTT (SEQ ID NO: 51) | 95292-97502 | 2211 |

TABLE 2-continued

| Exon | Exon length (bp) | Exon start to end* | Intronic sequence at acceptor splice site | Intronic sequence at donor splice site | Intron* | Intron length (bp) |
|---|---|---|---|---|---|---|
| 6 | 57 | 93509-93565 | GTGTGTAATTT TTTTTCTAG (SEQ ID NO: 52) | GTGAGCGAGTGT TAAATGAT (SEQ ID NO: 53) | 93566-95240 | 1675 |
| 7 | 93 | 75729-75821 | CCTTTCTTATTA TTTTTTAG (SEQ ID NO: 54) | GTTTGTTAGATAT TTAGGTG (SEQ ID NO: 55) | 75822-93508 | 17687 |
| 8 | 139 | 74569-74707 | TTCAGAATGAT TTACTGCAG (SEQ ID NO: 56) | GTTTGTGTCTTTT AATGAAT SEQ ID NO: 57) | 74708-75728 | 1021 |
| 9 | 128 | 68360-68487 | GGATTTGCTTT TACTTGTAG (SEQ ID NO: 58) | GTATCACTCTCAT TTCTAGA (SEQ ID NO: 59) | 68488-74568 | 6081 |
| 10 | 57 | 67188-67244 | ATCTTTTCTTT TTTTTTAG (SEQ ID NO: 60) | GTATTTATTAATG AGGAGGC (SEQ ID NO: 61) | 67245-68359 | 1115 |
| 11 | 72 | 65839-65910 | ATTTTGTACTTT GTCCAAAG (SEQ ID NO: 62) | GTAAGAGTTAAA TATTTTAA (SEQ ID NO: 63) | 65911-67187 | 1277 |
| 12 | 432 | 60629-61060 | TACTTCTCTATC TGATACAG (SEQ ID NO: 64) | GTAAGAACACCT TTAATTCA (SEQ ID NO: 65) | 61061-65838 | 4778 |
| 13 | 15 | 60124-60138 | TAATCTGCCTT TTGCCACAG (SEQ ID NO: 66) | GTAAGTTAAATT TTTTAAAA (SEQ ID NO: 67) | 60139-60628 | 490 |
| 14 | 444 | 57462-57905 | TTTTGATGCTTT TATTCTAG (SEQ ID NO: 68) | | 57906-60123 | 2218 |

*Start to end of exons and introns are referenced to genomic contig NT_010035, the orientation of both exons and introns are in complement to the genomic sequence of NT_010035 hydrophobic core for both the GTPase domain and the first half of the helical domain. The GTPase domain consists of an α/β structure with a nucleotide binding site. The active site is well-ordered and includes several residues that form biochemically sensible contacts with GTP. The P-loop (74GAFRKGKS81), DxxG (146DTQG) and RD motifs (217 RD) of atlastin are located in similar locations and conformations and are able to form similar interactions as the comparable residues in hGBP1. These observations suggest that atlastin contains a functional GTPase active site.

HSP-specific atlastin mutations alter amino acids located on the surface of the globular, amino-terminal region containing the conserved GTPase domain but do not occur in the predicted GTPase active site per se.

Through homology to hGBP1, atlastin is grouped in the dynamin family of large GTPases (reviewed in). Although the present invention is not limited to any particular theory, it is believed that dynamins play essential roles in a wide variety of vesicle trafficking events during formation of clathrin-coated vesicles from the plasma membrane, receptor-mediated endocytosis, and endosome trafficking to the trans-Golgi network. This may have has important relevance for neurotransmission and the action of neurotophic factors. Dynamins are essential for rapid and efficient recycling of synaptic vesicles, a critical process for neurotransmission and maintenance of synaptic membrane morphology. In addition, dynamins have been implicated in the maintenance and distribution of mitochondria; and have been found to associate with cytoskeletal elements including actin and microtubules.

Example 7

Methodology for atlastin gene diagnosis. Atlastin's coding sequence is divided into a number of separate exons. Mutations in these exons cause spastic paraplegia. Detection of these mutations is the basis of atlastin gene diagnosis. We have determined the atlastin's gene organization (intron-exon boundaries; see Table 2). Polymerase chain reaction (PCR) will be used to amplify each atlastin exon each. Each exon will then be amplified (to have a sufficient abundance for DNA sequencing) and then automated DNA sequencing will be used to determine the DNA sequence of the atlastin exon. The DNA sequence from a patient are compared to those of normal control subjects (i.e., the wildtype atlastin gene, SEQ ID NO:1).

As is evident from the foregoing, the present invention contemplates novel compositions and methods for research, diagnosis and treatment of Hereditary Spastic Paraplegia and related disorders.

We claim:

1. An isolated nucleic acid sequence encoding a human atlastin protein, wherein the nucleic acid sequence comprises a sequence selected from the group consisting of SEQ ID NO: 1 and the exact complementary sequence of SEQ ID NO: 1.

2. The isolated nucleic acid sequence of claim 1, wherein the sequence is operably linked to a heterologous promoter.

3. The isolated nucleic acid sequence of claim 2, wherein the sequence is contained within a vector.

4. An isolated nucleic acid sequence comprising SEQ ID NO: 1.

5. The isolated nucleic acid sequence of claim 4, wherein the sequence is operably linked to a heterologous promoter.

6. The isolated nucleic acid sequence of claim 5, wherein the sequence is contained within a vector.

7. An isolated nucleic acid sequence encoding a human atlastin protein wherein said human atlastin protein comprises the amino acid sequence of SEQ ID NO: 2.

* * * * *

UNITED STATES PATENT AND TRADEMARK OFFICE
CERTIFICATE OF CORRECTION

PATENT NO. : 7,649,088 B2  Page 1 of 1
APPLICATION NO. : 11/523305
DATED : January 19, 2010
INVENTOR(S) : Fink et al.

It is certified that error appears in the above-identified patent and that said Letters Patent is hereby corrected as shown below:

Item (73) on the Title Page of the patent:

"(73) Assignee: The Regents of the University of Michigan, Ann Arbor, MI (US)"

should read:

(73) Assignee: The Regents of the University of Michigan, Ann Arbor, MI (US)--, and the United States Government as represented by the Department of Veterans Affairs, Washington, D.C. (US)--

Signed and Sealed this
Thirty-first Day of January, 2012

David J. Kappos
*Director of the United States Patent and Trademark Office*

SEQUENCE LISTING

<160> NUMBER OF SEQ ID NOS: 68

<210> SEQ ID NO 1
<211> LENGTH: 2205
<212> TYPE: DNA
<213> ORGANISM: Homo sapiens
<220> FEATURE:
<221> NAME/KEY: CDS
<222> LOCATION: (169)..(1842)

<400> SEQUENCE: 1

```
ccctttcct ccccactcct tcccaccagc gccacagcaa catcctcaga gtctgagcga        60
actgcgccca gcgcgggcac ggagcctccc accgccagca acctgcggcc ccggagaagg      120
cagcgagcgc agtgacagcg cctcaccgcc accagctcct ggaccacc atg gcc aag      177
                                                    Met Ala Lys
                                                      1 aac cgc agg gac aga aac agt tgg ggt gga ttt tcg gaa aag aca tat       225
Asn Arg Arg Asp Arg Asn Ser Trp Gly Gly Phe Ser Glu Lys Thr Tyr
      5                  10                  15 gaa tgg agc tca gaa gag gag gag cca gtg aaa aag gca gga cca gtc       273
Glu Trp Ser Ser Glu Glu Glu Glu Pro Val Lys Lys Ala Gly Pro Val
 20                  25                  30                  35 caa gtc ctc att gtc aaa gat gac cat tcc ttt gag tta gat gaa act       321
Gln Val Leu Ile Val Lys Asp Asp His Ser Phe Glu Leu Asp Glu Thr
                 40                  45                  50 gca tta aat cgg atc ctt ctc tcg gag gct gtc aga gac aag gag gtt       369
Ala Leu Asn Arg Ile Leu Leu Ser Glu Ala Val Arg Asp Lys Glu Val
             55                  60                  65 gtt gct gta tct gtt gct gga gca ttt aga aaa gga aaa tca ttc ctg       417
Val Ala Val Ser Val Ala Gly Ala Phe Arg Lys Gly Lys Ser Phe Leu
         70                  75                  80 atg gac ttc atg ttg aga tac atg tac aac cag gaa tca gtt gat tgg       465
Met Asp Phe Met Leu Arg Tyr Met Tyr Asn Gln Glu Ser Val Asp Trp
 85                  90                  95 gtt gga gac tac aat gaa cca ttg act ggt ttt tca tgg aga ggt gga       513
Val Gly Asp Tyr Asn Glu Pro Leu Thr Gly Phe Ser Trp Arg Gly Gly
100                 105                 110                 115 tct gaa cga gag acc aca gga att cag ata tgg agt gaa atc ttc ctt       561
Ser Glu Arg Glu Thr Thr Gly Ile Gln Ile Trp Ser Glu Ile Phe Leu
                120                 125                 130 atc aat aaa cct gat ggt aaa aag gtt gca gtg tta ttg atg gat act       609
Ile Asn Lys Pro Asp Gly Lys Lys Val Ala Val Leu Leu Met Asp Thr
            135                 140                 145 cag gga acc ttt gat agt cag tca act ttg aga gat tca gcc aca gta       657
Gln Gly Thr Phe Asp Ser Gln Ser Thr Leu Arg Asp Ser Ala Thr Val
        150                 155                 160 ttt gcc ctt agc aca atg atc agc tca ata cag gta tat aac tta tcc       705
Phe Ala Leu Ser Thr Met Ile Ser Ser Ile Gln Val Tyr Asn Leu Ser
    165                 170                 175 caa aat gtc cag gag gat gat ctt cag cac ctc cag ctt ttc act gag       753
Gln Asn Val Gln Glu Asp Asp Leu Gln His Leu Gln Leu Phe Thr Glu
180                 185                 190                 195 tat ggc aga ctg gca atg gag gaa aca ttc ctg aag cca ttt cag agt       801
Tyr Gly Arg Leu Ala Met Glu Glu Thr Phe Leu Lys Pro Phe Gln Ser
                200                 205                 210 ctg ata ttt ctt gtt cga gac tgg agt ttc cca tac gaa ttt tca tat       849
Leu Ile Phe Leu Val Arg Asp Trp Ser Phe Pro Tyr Glu Phe Ser Tyr
            215                 220                 225
```

| | | |
|---|---|---|
| gga gcc gat ggt ggt gcc aaa ttc ttg gaa aaa cgc ctc aag gtc tca<br>Gly Ala Asp Gly Gly Ala Lys Phe Leu Glu Lys Arg Leu Lys Val Ser<br>230                              235                            240 | | 897 |
| ggg aac cag cat gaa gaa cta cag aac gtc aga aaa cac atc cat tcc<br>Gly Asn Gln His Glu Glu Leu Gln Asn Val Arg Lys His Ile His Ser<br>    245                         250                        255 | | 945 |
| tgt ttc acc aac att tcc tgt ttt ctg cta cct cat cct ggc tta aaa<br>Cys Phe Thr Asn Ile Ser Cys Phe Leu Leu Pro His Pro Gly Leu Lys<br>260                              265                        270                        275 | | 993 |
| gta gct acc aat cca aac ttt gat gga aaa ttg aaa gaa ata gat gat<br>Val Ala Thr Asn Pro Asn Phe Asp Gly Lys Leu Lys Glu Ile Asp Asp<br>                    280                        285                        290 | | 1041 |
| gaa ttc atc aaa aac ttg aaa ata ctg att cct tgg cta ctt agt ccc<br>Glu Phe Ile Lys Asn Leu Lys Ile Leu Ile Pro Trp Leu Leu Ser Pro<br>              295                        300                        305 | | 1089 |
| gag agc cta gat att aaa gag atc aat ggg aat aaa atc acc tgc cgg<br>Glu Ser Leu Asp Ile Lys Glu Ile Asn Gly Asn Lys Ile Thr Cys Arg<br>        310                        315                        320 | | 1137 |
| ggt ctg gtg gag tac ttc aag gct tat ata aag atc tat caa ggt gaa<br>Gly Leu Val Glu Tyr Phe Lys Ala Tyr Ile Lys Ile Tyr Gln Gly Glu<br>325                              330                        335 | | 1185 |
| gaa tta cca cat ccc aaa tcc atg tta cag gcc aca gca gaa gct aac<br>Glu Leu Pro His Pro Lys Ser Met Leu Gln Ala Thr Ala Glu Ala Asn<br>340                              345                        350                        355 | | 1233 |
| aat tta gca gcc gtg gca act gcc aag gac aca tac aac aaa aaa atg<br>Asn Leu Ala Ala Val Ala Thr Ala Lys Asp Thr Tyr Asn Lys Lys Met<br>                    360                        365                        370 | | 1281 |
| gaa gag att tgt ggt ggt gac aaa cca ttt ctg gcc cca aat gac ttg<br>Glu Glu Ile Cys Gly Gly Asp Lys Pro Phe Leu Ala Pro Asn Asp Leu<br>              375                        380                        385 | | 1329 |
| cag acc aaa cac ctg caa ctt aag gaa gaa tct gtg aag cta ttc cga<br>Gln Thr Lys His Leu Gln Leu Lys Glu Glu Ser Val Lys Leu Phe Arg<br>390                              395                        400 | | 1377 |
| ggg gtg aag aag atg ggt ggg gaa gaa ttt agc cgg cgt tac ctg cag<br>Gly Val Lys Lys Met Gly Gly Glu Glu Phe Ser Arg Arg Tyr Leu Gln<br>    405                         410                        415 | | 1425 |
| cag ttg gag agt gaa ata gat gaa ctt tac atc caa tat atc aag cac<br>Gln Leu Glu Ser Glu Ile Asp Glu Leu Tyr Ile Gln Tyr Ile Lys His<br>420                              425                        430                        435 | | 1473 |
| aat gat agc aaa aat atc ttc cat gca gct cgt acc cca gcc aca ctg<br>Asn Asp Ser Lys Asn Ile Phe His Ala Ala Arg Thr Pro Ala Thr Leu<br>                    440                        445                        450 | | 1521 |
| ttt gta gtc atc ttt atc aca tat gtg att gct ggt gtg act gga ttc<br>Phe Val Val Ile Phe Ile Thr Tyr Val Ile Ala Gly Val Thr Gly Phe<br>              455                        460                        465 | | 1569 |
| att ggt ttg gac atc ata gct agc cta tgc aat atg ata atg gga ctg<br>Ile Gly Leu Asp Ile Ile Ala Ser Leu Cys Asn Met Ile Met Gly Leu<br>                    470                        475                        480 | | 1617 |
| acc ctt atc acc ctg tgc act tgg gca tat atc cgg tac tct gga gaa<br>Thr Leu Ile Thr Leu Cys Thr Trp Ala Tyr Ile Arg Tyr Ser Gly Glu<br>485                              490                        495 | | 1665 |
| tac cga gag ctg gga gct gta ata gac cag gtg gct gca gct ctg tgg<br>Tyr Arg Glu Leu Gly Ala Val Ile Asp Gln Val Ala Ala Ala Leu Trp<br>500                              505                        510                        515 | | 1713 |
| gac cag gga agt aca aat gag gct ttg tac aag ctt tac agt gca gca<br>Asp Gln Gly Ser Thr Asn Glu Ala Leu Tyr Lys Leu Tyr Ser Ala Ala<br>                    520                        525                        530 | | 1761 |
| gca acc cac aga cat ctg tat cat caa gct ttc cct aca cca aag tcg<br>Ala Thr His Arg His Leu Tyr His Gln Ala Phe Pro Thr Pro Lys Ser<br>              535                        540                        545 | | 1809 |

-continued

```
gaa tct act gaa caa tca gaa aag aaa aaa atg taatgcaaat tttaagaaat      1862
Glu Ser Thr Glu Gln Ser Glu Lys Lys Lys Met
            550                 555 acaggtgcat gaccaattgt caattaaata ttcagtttta tgtctccatg caaacattca      1922
aagtgcttcc atcagaacgg agtaaaatac taaacacctc tgaagactgc aaactggatt      1982
agttctttta cttcagtgtt taataagcag atgtatgtat gcatggttat actattttgt      2042
taacatgtac aatttcctga ttttttcttca aaaatgctgt tataaagtat ttgtctattt     2102
atgataacag tacacgtgtt ctgcttgaat ttactaaatt ctactactgg gttataatta     2162
aatcatgtga tattccaaaa aaaaaaaaaa aaaaaaaaa aaa                         2205

<210> SEQ ID NO 2
<211> LENGTH: 558
<212> TYPE: PRT
<213> ORGANISM: Homo sapiens

<400> SEQUENCE: 2

Met Ala Lys Asn Arg Arg Asp Arg Asn Ser Trp Gly Gly Phe Ser Glu
1               5                   10                  15

Lys Thr Tyr Glu Trp Ser Ser Glu Glu Glu Pro Val Lys Lys Ala
            20                  25                  30

Gly Pro Val Gln Val Leu Ile Val Lys Asp Asp His Ser Phe Glu Leu
        35                  40                  45

Asp Glu Thr Ala Leu Asn Arg Ile Leu Leu Ser Glu Ala Val Arg Asp
    50                  55                  60

Lys Glu Val Val Ala Val Ser Val Ala Gly Ala Phe Arg Lys Gly Lys
65                  70                  75                  80

Ser Phe Leu Met Asp Phe Met Leu Arg Tyr Met Tyr Asn Gln Glu Ser
                85                  90                  95

Val Asp Trp Val Gly Asp Tyr Asn Glu Pro Leu Thr Gly Phe Ser Trp
            100                 105                 110

Arg Gly Gly Ser Glu Arg Glu Thr Thr Gly Ile Gln Ile Trp Ser Glu
        115                 120                 125

Ile Phe Leu Ile Asn Lys Pro Asp Gly Lys Lys Val Ala Val Leu Leu
    130                 135                 140

Met Asp Thr Gln Gly Thr Phe Asp Ser Gln Ser Thr Leu Arg Asp Ser
145                 150                 155                 160

Ala Thr Val Phe Ala Leu Ser Thr Met Ile Ser Ser Ile Gln Val Tyr
                165                 170                 175

Asn Leu Ser Gln Asn Val Gln Glu Asp Asp Leu Gln His Leu Gln Leu
            180                 185                 190

Phe Thr Glu Tyr Gly Arg Leu Ala Met Glu Glu Thr Phe Leu Lys Pro
        195                 200                 205

Phe Gln Ser Leu Ile Phe Leu Val Arg Asp Trp Ser Phe Pro Tyr Glu
    210                 215                 220

Phe Ser Tyr Gly Ala Asp Gly Gly Ala Lys Phe Leu Glu Lys Arg Leu
225                 230                 235                 240

Lys Val Ser Gly Asn Gln His Glu Glu Leu Gln Asn Val Arg Lys His
                245                 250                 255

Ile His Ser Cys Phe Thr Asn Ile Ser Cys Phe Leu Leu Pro His Pro
            260                 265                 270

Gly Leu Lys Val Ala Thr Asn Pro Asn Phe Asp Gly Lys Leu Lys Glu
        275                 280                 285
```

```
Ile Asp Asp Glu Phe Ile Lys Asn Leu Lys Ile Leu Ile Pro Trp Leu
            290                 295                 300
Leu Ser Pro Glu Ser Leu Asp Ile Lys Glu Ile Asn Gly Asn Lys Ile
305                 310                 315                 320
Thr Cys Arg Gly Leu Val Glu Tyr Phe Lys Ala Tyr Ile Lys Ile Tyr
                325                 330                 335
Gln Gly Glu Glu Leu Pro His Pro Lys Ser Met Leu Gln Ala Thr Ala
            340                 345                 350
Glu Ala Asn Asn Leu Ala Ala Val Ala Thr Ala Lys Asp Thr Tyr Asn
        355                 360                 365
Lys Lys Met Glu Glu Ile Cys Gly Gly Asp Lys Pro Phe Leu Ala Pro
370                 375                 380
Asn Asp Leu Gln Thr Lys His Leu Gln Leu Lys Glu Glu Ser Val Lys
385                 390                 395                 400
Leu Phe Arg Gly Val Lys Lys Met Gly Gly Glu Glu Phe Ser Arg Arg
                405                 410                 415
Tyr Leu Gln Gln Leu Glu Ser Glu Ile Asp Glu Leu Tyr Ile Gln Tyr
            420                 425                 430
Ile Lys His Asn Asp Ser Lys Asn Ile Phe His Ala Ala Arg Thr Pro
        435                 440                 445
Ala Thr Leu Phe Val Val Ile Phe Ile Thr Tyr Val Ile Ala Gly Val
450                 455                 460
Thr Gly Phe Ile Gly Leu Asp Ile Ile Ala Ser Leu Cys Asn Met Ile
465                 470                 475                 480
Met Gly Leu Thr Leu Ile Thr Leu Cys Thr Trp Ala Tyr Ile Arg Tyr
                485                 490                 495
Ser Gly Glu Tyr Arg Glu Leu Gly Ala Val Ile Asp Gln Val Ala Ala
            500                 505                 510
Ala Leu Trp Asp Gln Gly Ser Thr Asn Glu Ala Leu Tyr Lys Leu Tyr
        515                 520                 525
Ser Ala Ala Ala Thr His Arg His Leu Tyr His Gln Ala Phe Pro Thr
530                 535                 540
Pro Lys Ser Glu Ser Thr Glu Gln Ser Glu Lys Lys Met
545                 550                 555

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6
<211> LENGTH: 21
<212> TYPE: DNA
<213> ORGANISM: Artificial Sequence
<220> FEATURE:
<223> OTHER INFORMATION: Synthetic
```

<400> SEQUENCE: 6
acttcagcct aggcgacaga g                                              21

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
aatggtagaa gcttaaatt                                                 19

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8
cagggaacca gcatgaagaa cta                                            23

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
ccccggcagg tgattttatt                                                20

<210> SEQ ID NO 10
<211> LENGTH: 18
<212> TYPE: DNA
<213> ORGANISM: Artificial Sequence
<220> FEATURE:
<223> OTHER INFORMATION: Synthetic

<400> SEQUENCE: 10
ctcgttcaga tccacctc                                                  18

<210> SEQ ID NO 11
<211> LENGTH: 26
<212> TYPE: DNA
<213> ORGANISM: Artificial Sequence
<220> FEATURE:
<223> OTHER INFORMATION: Synthetic

<400> SEQUENCE: 11 ccttttcac tggctcctct cttctg                                          26

<210> SEQ ID NO 12
<211> LENGTH: 31
<212> TYPE: DNA
<213> ORGANISM: Artificial Sequence
<220> FEATURE:
<223> OTHER INFORMATION: Synthetic

<400> SEQUENCE: 12
ctccagcaac agatacagca acaacctcct t                                   31

<210> SEQ ID NO 13

```
<210> SEQ ID NO 13
<211> LENGTH: 19
<212> TYPE: DNA
<213> ORGANISM: Artificial Sequence
<220> FEATURE:
<223> OTHER INFORMATION: Synthetic

<400> SEQUENCE: 13
cccttggccc tccctgtct                                          19

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
gggggtgctg tttatttgtt t                                       21

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
gtccccaaag cactgaggtt                                         20

<210> SEQ ID NO 16
<211> LENGTH: 23
<212> TYPE: DNA
<213> ORGANISM: Artificial Sequence
<220> FEATURE:
<223> OTHER INFORMATION: Synthetic

<400> SEQUENCE: 16
cttggcactt tgagatgatt agc                                     23

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
gaaaattggt ctgtgtagtt                                         20

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
aagaggagga gccagtgaaa a                                       21

<210> SEQ ID NO 19
<211> LENGTH: 22
<212> TYPE: DNA
<213> ORGANISM: Artificial Sequence
<220> FEATURE:
<223> OTHER INFORMATION: Synthetic

<400> SEQUENCE: 19
```

```
gttataattt cgcctactct ga                                              22

<210> SEQ ID NO 20
<211> LENGTH: 17
<212> TYPE: DNA
<213> ORGANISM: Artificial Sequence
<220> FEATURE:
<223> OTHER INFORMATION: Synthetic

<400> SEQUENCE: 20
gatggttgct cctctgt                                                    17

<210> SEQ ID NO 21
<211> LENGTH: 18
<212> TYPE: DNA
<213> ORGANISM: Artificial Sequence
<220> FEATURE:
<223> OTHER INFORMATION: Synthetic

<400> SEQUENCE: 21
ttctaaccaa agcagtca                                                   18

<210> SEQ ID NO 22
<211> LENGTH: 18
<212> TYPE: DNA
<213> ORGANISM: Artificial Sequence
<220> FEATURE:
<223> OTHER INFORMATION: Synthetic

<400> SEQUENCE: 22
atggcatgtg taagaaat                                                   18

<210> SEQ ID NO 23
<211> LENGTH: 19
<212> TYPE: DNA
<213> ORGANISM: Artificial Sequence
<220> FEATURE:
<223> OTHER INFORMATION: Synthetic

<400> SEQUENCE: 23
tgggccaata gttcctgtt                                                  19

<210> SEQ ID NO 24
<211> LENGTH: 24
<212> TYPE: DNA
<213> ORGANISM: Artificial Sequence
<220> FEATURE:
<223> OTHER INFORMATION: Synthetic

<400> SEQUENCE: 24
tcattgttca ttccttattg tctc                                            24

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25
ttcctcattt ccatctcatt ctat                                            24

<210> SEQ ID NO 26
<211> LENGTH: 21
<212> TYPE: DNA
```

```
<213> ORGANISM: Artificial Sequence
<220> FEATURE:
<223> OTHER INFORMATION: Synthetic

<400> SEQUENCE: 26
ttgcaggtgc taaagttctc t                                              21

<210> SEQ ID NO 27
<211> LENGTH: 19
<212> TYPE: DNA
<213> ORGANISM: Artificial Sequence
<220> FEATURE:
<223> OTHER INFORMATION: Synthetic

<400> SEQUENCE: 27
caccaaatga tccaacaga                                                 19

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
ggcaccttaa agtcctcata                                                20

<210> SEQ ID NO 29
<211> LENGTH: 23
<212> TYPE: DNA
<213> ORGANISM: Artificial Sequence
<220> FEATURE:
<223> OTHER INFORMATION: Synthetic

<400> SEQUENCE: 29
atacatccag cgcccataga atc                                            23

<210> SEQ ID NO 30
<211> LENGTH: 24
<212> TYPE: DNA
<213> ORGANISM: Artificial Sequence
<220> FEATURE:
<223> OTHER INFORMATION: Synthetic

<400> SEQUENCE: 30
ttagtagcag ccctgtcgtg tcat                                           24

<210> SEQ ID NO 31
<211> LENGTH: 24
<212> TYPE: DNA
<213> ORGANISM: Artificial Sequence
<220> FEATURE:
<223> OTHER INFORMATION: Synthetic

<400> SEQUENCE: 31
ctcaagataa aagggacaa taat                                            24

<210> SEQ ID NO 32
<211> LENGTH: 19
<212> TYPE: DNA
<213> ORGANISM: Artificial Sequence
<220> FEATURE:
<223> OTHER INFORMATION: Synthetic

<400> SEQUENCE: 32
gggaggaaat gggggagat                                                 19
```

<210> SEQ ID NO 33
<211> LENGTH: 22
<212> TYPE: DNA
<213> ORGANISM: Artificial Sequence
<220> FEATURE:
<223> OTHER INFORMATION: Synthetic

<400> SEQUENCE: 33
tgaacacata aataggtaaa gt                                          22

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
cagattggca gacagagatg                                             20

<210> SEQ ID NO 35
<211> LENGTH: 22
<212> TYPE: DNA
<213> ORGANISM: Artificial Sequence
<220> FEATURE:
<223> OTHER INFORMATION: Synthetic

<400> SEQUENCE: 35
gttgcatgaa ggatactggt tt                                          22

<210> SEQ ID NO 36
<211> LENGTH: 24
<212> TYPE: DNA
<213> ORGANISM: Artificial Sequence
<220> FEATURE:
<223> OTHER INFORMATION: Synthetic

<400> SEQUENCE: 36
aattattttg aggactttgg tttc                                        24

<210> SEQ ID NO 37
<211> LENGTH: 18
<212> TYPE: DNA
<213> ORGANISM: Artificial Sequence
<220> FEATURE:
<223> OTHER INFORMATION: Synthetic

<400> SEQUENCE: 37
gtgtgctgaa tttagttg                                               18

<210> SEQ ID NO 38
<211> LENGTH: 18
<212> TYPE: DNA
<213> ORGANISM: Artificial Sequence
<220> FEATURE:
<223> OTHER INFORMATION: Synthetic

<400> SEQUENCE: 38 gataggggt ggaaagat                                                18

<210> SEQ ID NO 39
<211> LENGTH: 27
<212> TYPE: DNA
<213> ORGANISM: Artificial Sequence
<220> FEATURE:

```
<223> OTHER INFORMATION: Synthetic

<400> SEQUENCE: 39
ttctacacat tcatgaaaca aatactg                                            27

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
cacaatgggg aatgaatgaa g                                                  21

<210> SEQ ID NO 41
<211> LENGTH: 21
<212> TYPE: DNA
<213> ORGANISM: Artificial Sequence
<220> FEATURE:
<223> OTHER INFORMATION: Synthetic

<400> SEQUENCE: 41
tttataacag cattttgaa g                                                   21

<210> SEQ ID NO 42
<211> LENGTH: 18
<212> TYPE: DNA
<213> ORGANISM: Artificial Sequence
<220> FEATURE:
<223> OTHER INFORMATION: Synthetic

<400> SEQUENCE: 42
acacattgag gagttgaa                                                      18

<210> SEQ ID NO 43
<211> LENGTH: 20
<212> TYPE: DNA
<213> ORGANISM: Homo sapiens

<400> SEQUENCE: 43
gtgagtagca aatgagaact                                                    20

<210> SEQ ID NO 44
<211> LENGTH: 20
<212> TYPE: DNA
<213> ORGANISM: Homo sapiens

<400> SEQUENCE: 44
gtcactgctc tgttcaacag                                                    20

<210> SEQ ID NO 45
<211> LENGTH: 20
<212> TYPE: DNA
<213> ORGANISM: Homo sapiens

<400> SEQUENCE: 45
gtatgcagga agtactttaa                                                    20

<210> SEQ ID NO 46
<211> LENGTH: 20
<212> TYPE: DNA
<213> ORGANISM: Homo sapiens

<400> SEQUENCE: 46
```

-continued tagactttat cattttatag 20

<210> SEQ ID NO 47
<211> LENGTH: 20
<212> TYPE: DNA
<213> ORGANISM: Homo sapiens

<400> SEQUENCE: 47
gtatgatgct aacttcctaa 20

<210> SEQ ID NO 48
<211> LENGTH: 20
<212> TYPE: DNA
<213> ORGANISM: Homo sapiens

<400> SEQUENCE: 48
tttactcttc ttgcctgtag 20

<210> SEQ ID NO 49
<211> LENGTH: 20
<212> TYPE: DNA
<213> ORGANISM: Homo sapiens

<400> SEQUENCE: 49
gtatgaaata agcccatttt 20

<210> SEQ ID NO 50
<211> LENGTH: 20
<212> TYPE: DNA
<213> ORGANISM: Homo sapiens

<400> SEQUENCE: 50
aattttattt ctttatcaag 20

<210> SEQ ID NO 51
<211> LENGTH: 20
<212> TYPE: DNA
<213> ORGANISM: Homo sapiens

<400> SEQUENCE: 51
gtaacaatat ttattttctt 20

<210> SEQ ID NO 52
<211> LENGTH: 20
<212> TYPE: DNA
<213> ORGANISM: Homo sapiens

<400> SEQUENCE: 52
gtgtgtaatt tttttctag 20

<210> SEQ ID NO 53
<211> LENGTH: 20
<212> TYPE: DNA
<213> ORGANISM: Homo sapiens

<400> SEQUENCE: 53
gtgagcgagt gttaaatgat 20

<210> SEQ ID NO 54
<211> LENGTH: 20
<212> TYPE: DNA
<213> ORGANISM: Homo sapiens

```
<400> SEQUENCE: 54
cctttcttat tatttttag                                              20

<210> SEQ ID NO 55
<211> LENGTH: 20
<212> TYPE: DNA
<213> ORGANISM: Homo sapiens

<400> SEQUENCE: 55
gtttgttaga tatttaggtg                                             20

<210> SEQ ID NO 56
<211> LENGTH: 20
<212> TYPE: DNA
<213> ORGANISM: Homo sapiens

<400> SEQUENCE: 56
ttcagaatga tttactgcag                                             20

<210> SEQ ID NO 57
<211> LENGTH: 20
<212> TYPE: DNA
<213> ORGANISM: Homo sapiens

<400> SEQUENCE: 57
gtttgtgtct tttaatgaat                                             20

<210> SEQ ID NO 58
<211> LENGTH: 20
<212> TYPE: DNA
<213> ORGANISM: Homo sapiens

<400> SEQUENCE: 58
ggatttgctt ttacttgtag                                             20

<210> SEQ ID NO 59
<211> LENGTH: 20
<212> TYPE: DNA
<213> ORGANISM: Homo sapiens

<400> SEQUENCE: 59
gtatcactct catttctaga                                             20

<210> SEQ ID NO 60
<211> LENGTH: 20
<212> TYPE: DNA
<213> ORGANISM: Homo sapiens

<400> SEQUENCE: 60 atcttttct tttttttag                                               20

<210> SEQ ID NO 61
<211> LENGTH: 20
<212> TYPE: DNA
<213> ORGANISM: Homo sapiens

<400> SEQUENCE: 61
gtatttatta atgaggaggc                                             20

<210> SEQ ID NO 62
<211> LENGTH: 20
<212> TYPE: DNA
<213> ORGANISM: Homo sapiens
```

```
<400> SEQUENCE: 62
attttgtact ttgtccaaag                                               20

<210> SEQ ID NO 63
<211> LENGTH: 20
<212> TYPE: DNA
<213> ORGANISM: Homo sapiens

<400> SEQUENCE: 63
gtaagagtta aatattttaa                                               20

<210> SEQ ID NO 64
<211> LENGTH: 20
<212> TYPE: DNA
<213> ORGANISM: Homo sapiens

<400> SEQUENCE: 64
tacttctcta tctgatacag                                               20

<210> SEQ ID NO 65
<211> LENGTH: 20
<212> TYPE: DNA
<213> ORGANISM: Homo sapiens

<400> SEQUENCE: 65
gtaagaacac ctttaattca                                               20

<210> SEQ ID NO 66
<211> LENGTH: 20
<212> TYPE: DNA
<213> ORGANISM: Homo sapiens

<400> SEQUENCE: 66
taatctgcct tttgccacag                                               20

<210> SEQ ID NO 67
<211> LENGTH: 20
<212> TYPE: DNA
<213> ORGANISM: Homo sapiens

<400> SEQUENCE: 67
gtaagttaaa ttttttaaaa                                               20

<210> SEQ ID NO 68
<211> LENGTH: 20
<212> TYPE: DNA
<213> ORGANISM: Homo sapiens

<400> SEQUENCE: 68
ttttgatgct tttattctag                                               20
```